United States Patent [19]

Albright et al.

[11] Patent Number: 5,189,023

[45] Date of Patent: Feb. 23, 1993

[54] RENIN INHIBITORS

[75] Inventors: Jay D. Albright, Nanuet; Fuk-Wah Sum, New City, both of N.Y.

[73] Assignee: American Cyanamid Company, Wayne, N.J.

[21] Appl. No.: 780,587

[22] Filed: Oct. 22, 1991

Related U.S. Application Data

[63] Continuation-in-part of Ser. No. 577,175, Sep. 4, 1990, abandoned.

[51] Int. Cl.$^5$ .............................................. A61K 37/00
[52] U.S. Cl. ...................................... 514/19; 514/18; 530/331; 260/998.2; 549/218
[58] Field of Search ................. 549/218; 514/19, 18; 260/998.2; 530/331

[56] References Cited

U.S. PATENT DOCUMENTS

| | | | |
|---|---|---|---|
| 4,168,267 | 2/1979 | Petrillo, Jr. | 548/413 |
| 4,316,896 | 2/1982 | Thorsett | 548/413 |
| 4,379,146 | 4/1983 | Greenlee et al. | 548/112 |
| 4,416,831 | 4/1983 | Petrillo, Jr. | 559/218 |
| 4,432,972 | 2/1984 | Karanewsky et al. | 549/218 |
| 4,590,178 | 5/1986 | Sakakibara et al. | 514/18 |
| 4,845,079 | 2/1989 | Luly et al. | 530/331 |
| 4,853,476 | 5/1989 | Petrakis | 549/221 |
| 4,885,292 | 12/1989 | Ryono et al. | 514/211 |
| 5,106,835 | 4/1992 | Albright et al. | 514/18 |

FOREIGN PATENT DOCUMENTS

| | | |
|---|---|---|
| 0117420 | 5/1984 | European Pat. Off. |
| 0231919 | 8/1987 | European Pat. Off. |
| 0309766 | 4/1989 | European Pat. Off. |
| 0401963 | 12/1990 | European Pat. Off. |
| 61-03790 | 2/1986 | Japan |
| 2106114 | 4/1983 | United Kingdom |

OTHER PUBLICATIONS

Burger, "Medicinal Chem." 2nd Ed., Interscience, New York 1960, pp. 565-601.

Denkewalter, "Progress in Drug Research", vol. 10, 1966 pp. 510-512.

Bolis, "Renin Inhibitors", J. Med. Chem. 1987, 30: pp. 1729-1737.

Haber, "Renin Inhibitors", J. Cardiovascular Pharm., pp. 554-558 (1987).

Primary Examiner—Ronald W. Griffin
Attorney, Agent, or Firm—Kenneth J. Dow

[57] ABSTRACT

Renin inhibiting compounds of the formula:

$$R_1 \!-\!\!\left(\!\!W\!-\!\overset{R_2}{\underset{*}{C}H}\!-\!\overset{O}{\overset{\|}{C}}\!\right)_{\!q}\!\!-\!\overset{R_4}{\underset{R_3}{C}}\!-\!\overset{}{\underset{*}{C}H}\!-\!\overset{O}{\overset{\|}{C}}\!-\!\overset{}{\underset{R_5}{N}}\!-\!\overset{R_6}{\underset{*}{C}H}\!-\!\overset{OH}{\underset{*}{C}H}\!-\!A$$

containing two α-amino acids or a single α-amino acid wherein $R_1$ is a phosphorus containing moiety, W is oxygen or $NR_3$ and A is a moiety selected from those of the formula:

$$\underset{Z}{\left\langle\!\!\!\phantom{\rule{1em}{0ex}}\!\!\!\right.}\!\!\!\!-\!\!(CH_2)_p;$$

wherein Z is O, S, SO, $SO_2$ and p is an integer from 1 to 2; and, when W is oxygen, A may also be a moiety of the formula $$\underset{O}{\left\langle\!\!\!\phantom{\rule{1em}{0ex}}\!\!\!\right.}\!\!\!\!-\!\!R; \quad \underset{S}{\left\langle\!\!\!\phantom{\rule{1em}{0ex}}\!\!\!\right.}\!\!\!\!-\!\!R$$

and analogs thereof which compounds inhibit the substrate-cleaving action of renin, pharmaceutical compositions containing these compounds, processes for producing the compounds and methods of treating hypertension which employ the novel renin inhibitors.

30 Claims, No Drawings

RENIN INHIBITORS

CROSS REFERENCE TO RELATED APPLICATION

This application is a continuation-in-part of application Ser. No. 07/577,175 filed Sep. 4, 1990, now abandoned.

FIELD OF THE INVENTION

This invention relates to new compounds containing two α-amino acids or a single α-amino acid which inhibit renin and are thus useful in treating hypertension.

BACKGROUND OF THE INVENTION

Renin is an endopeptidase which plays an important role in the control of blood pressure. The renin angiotensin system is a multiregulated proteolytic cascade in which renin cleaves the protein substrate angiotensinogen to give the relatively inactive decapeptide angiotensin I. Angiotensin converting enzyme (AOE) catalyses the removal of the terminal dipeptide from angiotensin I to form the highly active octapeptide angiotensin II which exhibits potent pressor activity. In addition to its direct vasoconstricting effect, angiotensin II also stimulates the adrenal cortex to release aldosterone, which leads to sodium retention and a rise in extraoellular fluid volume. Thus, the renin-angiotensin system plays a key role in the regulation of blood pressure and is implicated in some forms of hypertension.

In an effort to develop agents useful in the treatment of hypertension, compounds called ACE inhibitors have been developed which inhibit angiotensin I converting enzyme thereby blocking the generation of angiotensin II and its vasopressive effects; these include captopril and enalapril maleate. Similarly, effective inhibitors of renin have been sought which would reduce the release of angiotensin I and ultimately lead to a reduction in the circulating level of angiotensin II. Thus, renin inhibitors would be useful alternatives to ACE inhibitors as therapeutic agents in the treatment of hypertension and congestive heart failure.

A number of prior art reference have described peptide compounds that have activity as renin inhibitors. For example, Boger et al., Nature, 303, 81-84, (1983) describe peptide renin inhibitors containing the amino acid statine. See also Veber et al. U.S. Pat. Nos. 4,384,994 and 4,478,826. However, because these compounds are peptides, many of them are unsuitable for oral administration because of their proteolytic lability and poor absorption from the digestive tract. Smaller peptides that are better absorbed orally have proven to be poor inhibitors of renin. Recent efforts have been focused on formulating compounds which are effective orally yet retain high potency as inhibitors of human renin.

Recently, Iizuka and coworkers have described peptide renin inhibitors containing an unnatural amino acid, norstatine, (J. Med. Chem. vol. 31, 701-701, 1988) which are active orally.

Other compounds having renin inhibiting activity have been disclosed with involve modifications to the N-terminal units, for example, Luly et al. U.S. Pat. No. 4,826,815, Sham, et. al. U.S. Pat. No. 4,826,958, Iizuka et al. EP-0,206,807-A3, EP-0,190,891-A2, U.S. Pat. No.4,656,269 and Hanson et al. Biochem Biophys. Res. Comm., 160, 1-5 (1989). Certain modifications to the central amino acid structure have also been tried, see for example, Patchett et al. U.S. Pat. No. 4,839,357, and Bock et al. U.S. Pat. No. 4,663,310. Finally, modifications in the C-terminal substituents are disclosed in Boger et al. U.S. Pat. No. 4,782,043 and U.S. Pat. No. 4,885,292. The latter reference discloses compounds having heterocyclic nitrogen containing rings of 5 or 6 carbon atoms at the C-terminal unit.

The present invention relates to structurally novel renin inhibitors containing two α-amino acids or a single α-amino acid. The present compounds differ from the prior art in the novel C-terminal units and an N-terminal phosphinyl group.

SUMMARY OF THE INVENTION

This invention relates to new derivatives selected from those of general formula I,

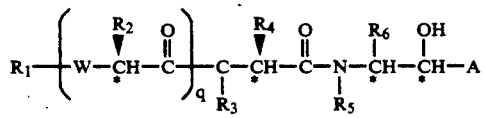

wherein $R_1$ is

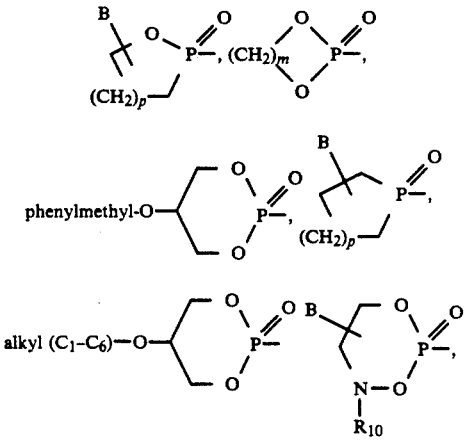

[alkyl($C_1$–$C_6$)O]

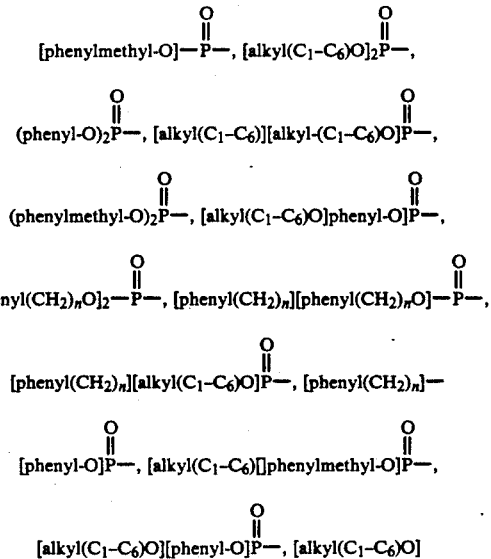

[phenylmethyl-O]—$\overset{O}{\underset{\|}{P}}$—, [alkyl($C_1$–$C_6$)O]$_2$$\overset{O}{\underset{\|}{P}}$—, (phenyl-O)$_2$$\overset{O}{\underset{\|}{P}}$—, [alkyl($C_1$–$C_6$)][alkyl-($C_1$–$C_6$)O]$\overset{O}{\underset{\|}{P}}$—, (phenylmethyl-O)$_2$$\overset{O}{\underset{\|}{P}}$—, [alkyl($C_1$–$C_6$)O]phenyl-O]$\overset{O}{\underset{\|}{P}}$—,

[phenyl($CH_2$)$_n$O]$_2$—$\overset{O}{\underset{\|}{P}}$—, [phenyl($CH_2$)$_n$][phenyl($CH_2$)$_n$O]—$\overset{O}{\underset{\|}{P}}$—,

[phenyl($CH_2$)$_n$][alkyl($C_1$–$C_6$)O]$\overset{O}{\underset{\|}{P}}$—, [phenyl($CH_2$)$_n$]—

[phenyl-O]$\overset{O}{\underset{\|}{P}}$—, [alkyl($C_1$–$C_6$)][phenylmethyl-O]$\overset{O}{\underset{\|}{P}}$—,

[alkyl($C_1$–$C_6$)O][phenyl-O]$\overset{O}{\underset{\|}{P}}$—, [alkyl($C_1$–$C_6$)O]

-continued

[alkyl($C_1$-$C_3$)$_2$N—(CH$_2$)$_n$O]—P(=O)—

[alkyl($C_1$-$C_6$)][alkyl($C_1$-$C_6$)]—P(=O)—,

[phenylmethyl-O][CH$_3$CONH(CH$_2$)$_n$O]P(=O)—,

[phenyl(CH$_2$)$_n$][CH$_3$CONH(CH$_2$)$_n$O]P(=O)—,

[phenyl(CH$_2$)$_n$][4-morpholino-CO(CH$_2$)$_n$OP(=O)—,

[phenyl-O][(phenylmethyl-OCONH)O]—P(=O),

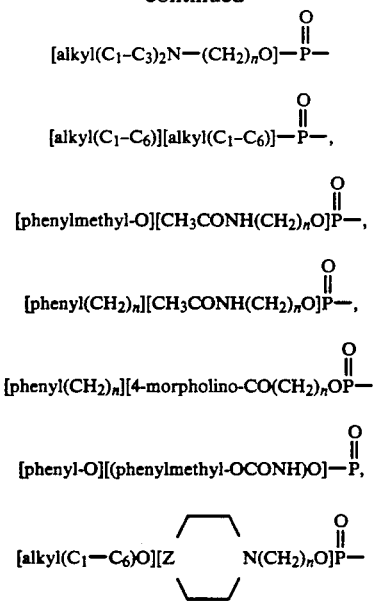

where
  Z is O, S, SO or SO$_2$;
  n is an integer from 1 to 4;
  m is an integer from 2 to 4, p is an integer from 1 to 2,
  B is phenylmethyl, cyclohexylmethyl, alkyl ($C_1$-$C_6$), $R_{10}$ is H, alkyl($C_1$-$C_3$), alkyl($C_1$-$C_3$)CO-, q is an integer from zero to one;
  $R_2$ is phenylmethyl, cyclohexylmethyl, —CH$_2$(2-thienyl), —CH$_2$(3-indolyl), 4-methoxybenzyl, —CH$_2$-naphthyl or lower alkyl($C_1$-$C_6$);
  $R_3$ is hydrogen or methyl;
  $R_4$ is alkyl($C_1$-$C_8$)(branched or unbranched), —(CH$_2$)$_n$—NH$_2$, phenylmethyl, cyclohexylmethyl, —X-alkyl($C_1$-$C_8$) (branched or unbranched), X-cyclohexyl, —(CH$_2$)$_n$—X-alkyl($C_1$-$C_3$), X—CH$_2$CH$_2$N[alkyl($C_1$-$C_3$)]$_2$ (where X is —O— or —S—) and moieties of the formulae:

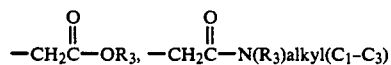

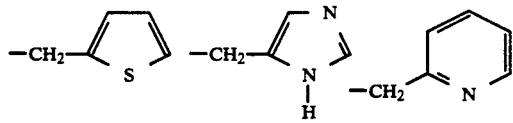

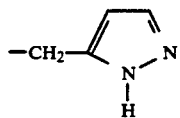

$R_5$ is hydrogen or methyl; $R_6$ is alkyl ($C_1$-$C_6$), phenylmethyl, cyclohexylmethyl or

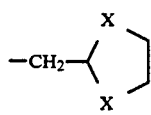

W is —O— or —N—$R_3$ and A is selected from:

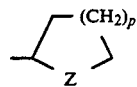

where Z is O, S, SO, SO$_2$ and p is an integer from 1 to 2, and when W is —O— then A may also be

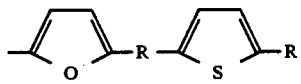

wherein R is selected from the group consisting of Cl, Br, F, —CO-lower alkyl($C_1$-$C_6$), —CO$_2$ lower alkyl($C_1$-$C_6$),

—CO$_2$H and lower alkyl($C_1$-$C_6$).

DETAILED DESCRIPTION OF THE INVENTION

Within the group of compounds defined by formula I, certain subgroups of compounds are preferred.

Preferred are compounds of formula I wherein q is an integer zero or one;

$R_1$ is

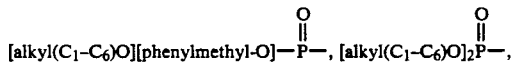

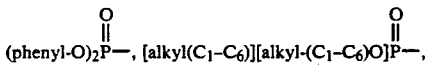

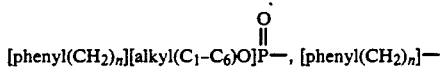

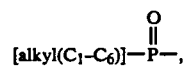

where
  n is an integer from 1 to 4;

$R_2$ is phenylmethyl, cyclohexylmethyl, 4-methoxybenzyl, —CH$_2$-naphthyl or lower alkyl(C$_1$–C$_6$);

$R_3$ is hydrogen or methyl;

$R_4$ is alkyl(C$_1$–C$_8$)(branched or unbranched), phenylmethyl, cyclohexylmethyl, and moieties of the formulae:

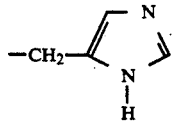

$R_5$ is hydrogen or methyl; $R_6$ is alkyl (C$_1$–C$_6$), phenylmethyl, cyclohexylmethyl;

W is —O— or —N—R$_3$ and A is selected from:

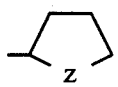

where Z is O, S, SO, SO$_2$.

The compounds of formula I are those compounds where the α-amino acids have the natural L configuration. Thus the compounds claimed are those compounds where the α-aminoacid unit or the α-hydroxy acid unit in formula I have the L configuration. Especially preferred in the C-terminal units are compounds where the C-terminal units are selected from those of formula II,

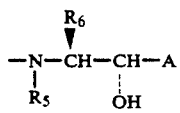

Formula II with an anti(threo) relationship between the amino group and the hydroxyl group. Most preferred of the 1-amino-2-hydroxy compounds of formula II are those diastereomers with the 1S configuration.

Most preferred of the compounds of formula I, wherein the C-terminal group is represented by formula II, are those compounds wherein $R_1$ is

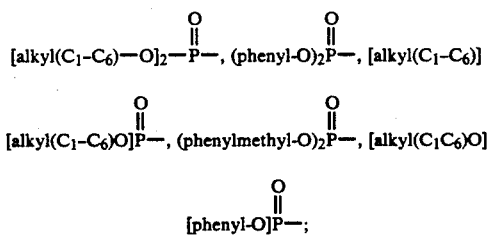

$R_2$ is phenylmethyl, (3-indolyl)CH$_2$, (4-methoxyphenyl)methyl, cyclohexylmethyl or CH$_2$-naphthyl; $R_3$ is hydrogen; $R_4$ is alkyl(C$_1$–C$_8$),

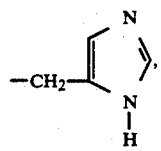

$R_5$ is hydrogen: $R_6$ is selected from the group consisting of alkyl(C$_1$–C$_6$) or cyclohexylmethyl

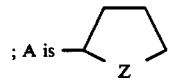

; A is where Z is O, S, SO, SO$_2$ and w is O or NR$_3$.

According to the present invention, the N-terminal unit in formula I has the S configuration as shown in formula III

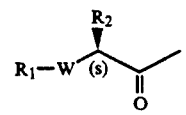

Formula III

The most preferred of the compounds of formula I, where q is zero and the C-terminal group is represented by formula II are those compounds wherein $R_1$ is

$R_3$ and $R_5$ are hydrogen;
$R_4$ is alkyl(C$_1$–C$_6$), O-alkyl(C$_1$–C$_6$), S-alkyl(C$_1$–C$_6$);
$R_6$ is cyclohexylmethyl; and
A is

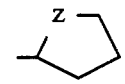

Included in this invention are compounds of the formula:

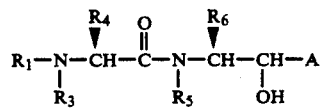

wherein
$R_1$ is

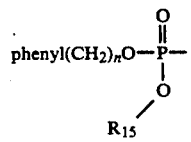

$R_3$ and $R_5$ are hydrogen;
$R_4$ is alkyl(C$_1$–C$_6$), or

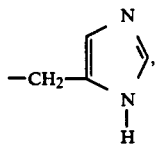

R₆ is cyclohexylmethyl;

R₁₅ is lower alkyl(C₁-C₃)NH(CH₂)$_n$—, [lower alkyl(-C₁-C₃)]₂N—(CH₂)$_n$—, phenyl(CH₂)$_n$—, Br—(CH₂)$_n$—, phenyl(CH₂)$_n$NH(CH₂)$_n$—, cyclohexyl(R₁₆—CH-)—NH(CH₂)$_n$—, 2-pyridinyl(CH₂)$_n$NH(CH₂)$_n$—, 3-pyridinyl(CH₂)$_n$NH(CH₂)$_n$—, 4-pyridinyl(CH₂)$_n$NH(CH₂)$_n$—,

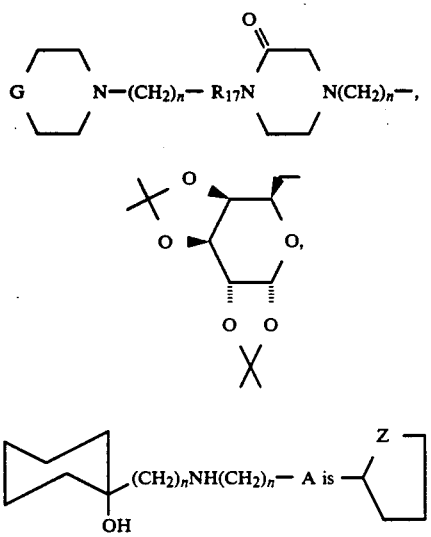

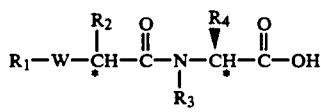

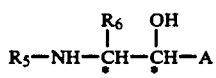

where Z is O, S, SO, SO₂, n is 2 or 3, G is O, S, SO, SO₂, NH—, CH₃CON—, R₁₆ is H or OH and R₁₇ is H or CH₃.

The products of formula I and the preferred subgroups can be prepared by various synthetic procedures.

For example, the products wherein q is one can be prepared by reacting an α-amino acid derivative of formula IV:

$$R_1-W-\overset{R_2}{\underset{*}{C}H}-\overset{O}{\overset{\|}{C}}-\overset{R_4}{\underset{R_3}{N}}-\overset{O}{\underset{*}{C}H}-\overset{O}{\overset{\|}{C}}-OH$$

Formula IV or its chemical equivalent with a 1-amino-2-hydroxy compound of formula v, $$R_5-NH-\overset{R_6}{\underset{*}{C}H}-\overset{OH}{\underset{*}{C}H}-A$$

Formula V

Thus a compound of formula IV is reacted with a peptide coupling reagent to convert the carboxyl group into an activated derivative which is then reacted with a compound of formula v, or its chemical equivalent to give the products of this invention.

Preferred peptide coupling reagents are those which do not cause racemization at the carbons designated with asterisks. For example, appropriate peptide coupling reagents are:
1) N,N'-Dicyclohexylcarbodiimide plus 1-hydroxybenzotriazole
2) Benzotriazol-1-yloxytris (dimethylamino)phosphonium hexafluorophosphate (BOP-reagent)
3) N,N'-Bis[2-oxo-3-oxazolidinyl]phosphorodiamidic chloride (BOP-Cl)
4) Diphenylphosphinyl chloride (DPP-Cl)
5) Diethoxyphosphoryl cyanide
6) 2-Chloro-1-methylpyridinium iodide
7) Phenyl dichlorophosphate plus imidazole Other peptide coupling reagents which may be used include N,N'-dicyclohexylcarbodiimide, with or without N-hydroxysuccinimide, 1-benzotriazolyl diethyl phosphate, 1-chloro-N,N-2-trimethyl-1-propen-1-amine, diphenyl phosphoryl azide, diethyl phosphorochloridate, phenyl phosphorochloridate, N,N-carboxyldiimidazole, isobutyl chloroformate plus N-methylmorpholine.

In the compounds of formula IV, where R₄ is 4-imidazolylmethyl, the imidazole nitrogen is blocked with an appropriate group such as tosyl, 2,4-dinitrophenyl, benzyl, or benzyloxymethyl, prior to coupling with compounds of formula V. A suitable blocking group is chosen so that conditions for its removal are compatible with other structural features in the product of formula I.

Alternatively a compound of formula IV is activated with an appropriate peptide coupling reagent and then reacted with a compound of formula VI in which the hydroxy group is protected with a removable blocking group y Suitable blocking groups are represented by trimethylsilyl, t-butyldimethylsilyl, tetrahydropyranyl, acetyl, benzoyl and the like. Removal of the hydroxyl blocking group then gives the compounds of formula I:

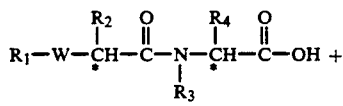

IV

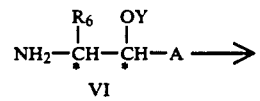

VI

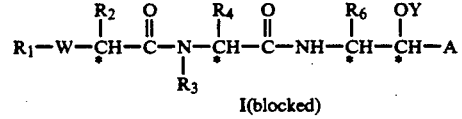

I(blocked)

The compounds of formula I may also be prepared by coupling sequentially N-blocked α-amino acids of formula VII (where R₉ is a N-blocking group such as tert-butoxy-carbonyl, benzyloxycarbonyl and the like) to compounds of formula VIII as shown in Scheme B. The derivatives (Formula IX) are then deblocked to give compounds of formula X which are coupled with the N-terminal unit to give compounds of formula XI, (Scheme B). The hydroxyl blocking group (Y) is then removed to afford compounds of formula I. The sequence of reactions may also be carried out wherein the blocking group (Y) is removed first and the derivatives of formula XII, containing a free hydroxyl group are coupled to the N-terminal unit of formula XIII. The coupling reactions (Scheme B) may also be carried out with the compounds of formula VIII wherein the hydroxyl group is not blocked (Y=H) to give derivatives IX(Y=H) and X(Y=H).

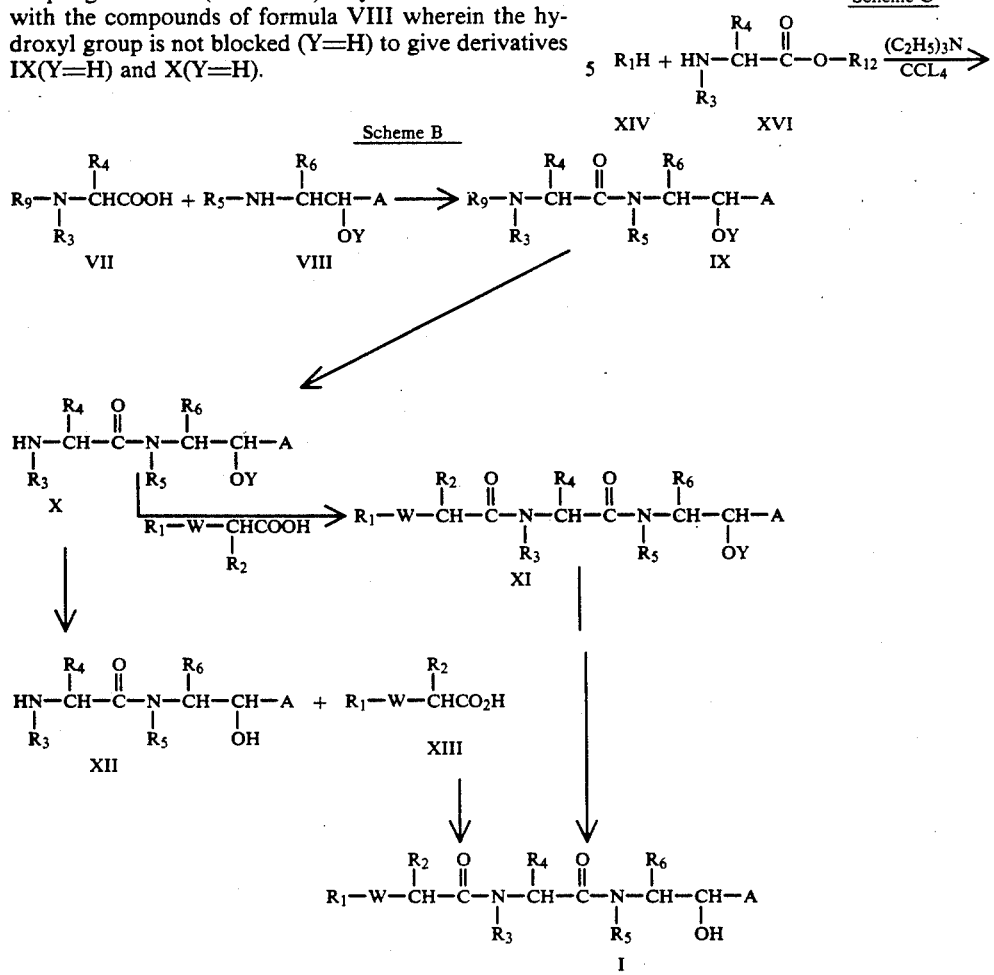

The compounds of formula I, where q is zero may be prepared according to Scheme C by reacting a C-terminal derivative of formula XII with a derivative of formula XIV where $R_1$ is a phosphorus containing derivative as previously defined. The products of this reaction are derivatives of formula XV which contain only one α-aminoacid. Alternatively, the phosphorus containing derivative $R_1$—H of formula XIV may be reacted with an α-amino acid ester of formula XVI, wherein $R_{12}$ is a removable ester blocking group, to give intermediates XVII. Hydrolysis of the ester function in intermediates XVIII and coupling of the acids derivatives XVII with the C-terminal unit of the formula V gives the products XV of formula I wherein q is zero.

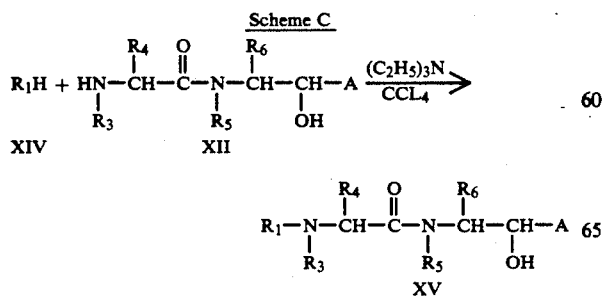

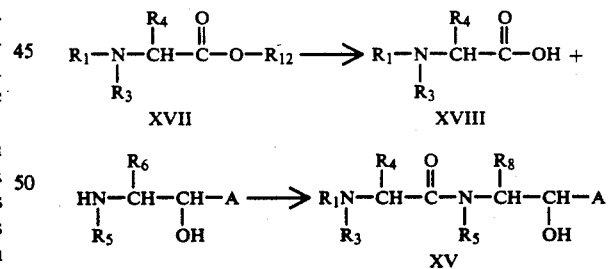

The compounds of formula I are active inhibitors of renin.

Renin is an endopeptidase which plays an important role in the control of blood pressure. The renin angiotensin system is a multiregulated proteolytic cascade in which renin cleaves the protein substrate angiotensinogen to give angiotensin I. Angiotensin converting enzyme (ACE) catalyses the removal of the terminal dipeptide from the decapeptide angiotensin I to form angiotensin II which exhibits potent pressor activity.

Renin is an aspartyl protease with high substrate specificity and is the first proteolytic step in the renin-angiotensin system which is involved in the control of blood pressure.

Renin inhibitors have been shown to lower blood pressure in primates, [J. Hypertension, 1, 399 (1983), J. Hypertension 1 (suppl 2), 189 (1983)] and in man, [Lancet II, 1486 (1983), Trans. Assoc. Am. Physicians, 96, 365 (1983), J. Hypertension, 3, 653 (1985)] and thus are potentially useful in the control of hypertension.

The novel compounds of formula I are new peptide renin inhibitors and are useful in the treatment of hypertension in warm-blooded animals, as established in the following test.

Radioimmunoassay Screen For Renin Inhibitors

The in vitro method for the screening of anti-renin compounds involves, first, angiotensin I generation, and second, the quantitation of the angiotensin I produced by radioimmunoassay.

Angiotensin I Generation

The incubation medium consisted of 20 μl of purified human plasma angiotensinogen (1); 10 μl of human kidney renin (2); 5 μl of phenylmethylsulfonyl fluoride; 10 μl of disodium EDTA (10 mM); 10 μl of antirenin compound ($5\times10^{-3}$, $5\times10^{-4}$, $5\times10^{-5}$) in dimethylformamide, or ethanol and a suitable amount of maleate buffer (77 mM, pH 6.0) to make a final volume of 500 μl. The reaction mixture is incubated for one hour at 37° C. and the enzymatic reaction is stopped by placing the tube in ice-cold water. The angiotensin I generated during the incubation is measured by a radioimmunoassay plasma renin activity kit (Clinical Assays, Inc.).

Radioimmunoassay Procedure

The incubation medium consisted of either 100 μl aliquots of the above reaction mixture or a standard amount of angiotensin I; 1000 μl of phosphate buffer (100 mM, pH$_{7.6}$) and 100 μl of ($^{125}$I)angiotensin in a gamma-coat, tube. After three hours of incubation at room temperature, the tubes are decanted, and the radioactivity of each tube is determined in a gamma counter. Duplicate determinations were performed for each incubation. The results are expressed in ng of angiotensin I generated per ml of generation medium per hour of incubation (ng/AI/ml/hr).

The results of this test on representative compounds of this invention appear in Table I, expressed as an IC$_{50}$.

(1) The human plasma angiotensinogen derived from the blood of a woman receiving oral contraceptive pills is purified by chromatography on a pepstatin-aminohexyl-agarose column.

(2) Human renin is prepared from human kidney.

TABLE I

Renin Inhibitors

| Compound | IC$_{50}$ Molar Concentration |
|---|---|
| (C$_2$H$_5$O)$_2$P(O)—O—CH(Ph)—C(O)—Leu—NH—[cyclohexyl, OH, furan] | $1.4 \times 10^{-7}$ |
| (C$_2$H$_5$O)$_2$P(O)—O—CH(Ph)—C(O)—Leu—NH—[cyclohexyl, OH, thiophene] | $2.9 \times 10^{-7}$ |
| (C$_2$H$_5$O)$_2$P(O)—O—CH(Ph)—C(O)—Leu—NH—[cyclohexyl, OH, tetrahydrofuran *(R,S)*] | $1.5 \times 10^{-9}$ |
| (C$_2$H$_5$O)$_2$P(O)—NH—CH(cyclohexyl)—C(O)—Leu—NH—[cyclohexyl, OH, tetrahydrofuran *(R,S)*] | $3.0 \times 10^{-9}$ |

TABLE I-continued
Renin Inhibitors

| Compound | IC$_{50}$ Molar Concentration |
|---|---|
| (C$_2$H$_5$O)$_2$P(=O)—PheLeu—NH—CH(CH$_2$-cyclohexyl)—CH(OH)—[tetrahydrofuran-2-yl *(R,S)] | $2.0 \times 10^{-10}$ |
| (EtO)$_2$P(=O)—O—CH(CH$_2$-cyclohexyl)—C(=O)—Leu—NH—CH(CH$_2$-cyclohexyl)—CH(OH)—[tetrahydrofuran-2-yl *(R,S)] | $3.5 \times 10^{-9}$ |
| (EtO)$_2$P(=O)—O—CH(CH$_2$Ph)—C(=O)—Leu—NH—CH(CH$_2$-cyclohexyl)—CH(OH)—[tetrahydrofuran-2-yl *(S)] | $3.0 \times 10^{-9}$ |
| (EtO)$_2$P(=O)—PheLeu—NH—CH(CH$_2$-cyclohexyl)—CH(OH)—[tetrahydrofuran-2-yl *(S)] | $1 \times 10^{-10}$ |
| (EtO)$_2$P(=O)—Leu—NH—CH(CH$_2$-cyclohexyl)—CH(OH)—[tetrahydrofuran-2-yl *(S)] | 37% Inhibition at $10^{-5}$M |
| Ph(CH$_2$)$_3$P(=O)(OCH$_3$)—Leu—NH—CH(CH$_2$-cyclohexyl)—CH(OH)—[tetrahydrofuran-2-yl *(S)] | $5.1 \times 10^{-8}$ |
| Ph(CH$_2$)$_3$P(=O)(OCH$_2$CH$_2$NHCOCH$_3$)—Leu—NH—CH(CH$_2$-cyclohexyl)—CH(OH)—[tetrahydrofuran-2-yl *(S)] | $3.3 \times 10^{-8}$ |

TABLE I-continued

Renin Inhibitors

| Compound | IC$_{50}$ Molar Concentration |
|---|---|
| (PhO)$_2$P(=O)—Leu—NH—CH(CH$_2$-cyclohexyl)—CH(OH)—CH(tetrahydrofuran) *(S) | $8.1 \times 10^{-6}$ |
| (PhCH$_2$O)$_2$P(=O)—Leu—NH—CH(CH$_2$-cyclohexyl)—CH(OH)—CH(tetrahydrofuran) *(S) | $2.7 \times 10^{-8}$ |
| PhCH$_2$O—C(=O)—NH—O—P(=O)(OPh)—Leu—NH—CH(CH$_2$-cyclohexyl)—CH(OH)—CH(tetrahydrofuran) *(S) | $1.8 \times 10^{-6}$ |
| (EtO)$_2$P(=O)—NH—CH(CH$_2$-cyclohexyl)—C(=O)—CH$_2$—Leu—NH—CH(CH$_2$-cyclohexyl)—CH(OH)—CH(tetrahydrofuran) *(S) | $1 \times 10^{-10}$ |
| (EtO)$_2$P(=O)—PheLeu—NH—CH(CH$_2$-cyclohexyl)—CH(OH)—CH(tetrahydrofuran) *(R) | $8.1 \times 10^{-9}$ |
| PhCH$_2$CH$_2$—O—P(=O)(O—CH$_2$CH$_2$—N(CH$_3$)$_2$)—Leu—NH—CH(CH$_2$-cyclohexyl)—CH(OH)—CH(tetrahydrofuran) · HCL | $6.4 \times 10^{-7}$ |

TABLE I-continued
Renin Inhibitors
| Compound | IC$_{50}$ Molar Concentration |
|---|---|
| 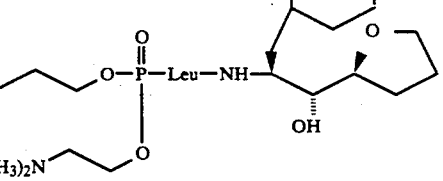 | $5.5 \times 10^{-7}$ |
| 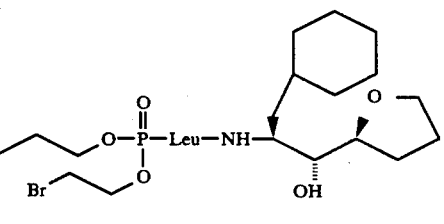 | $1.4 \times 10^{-7}$ |
| 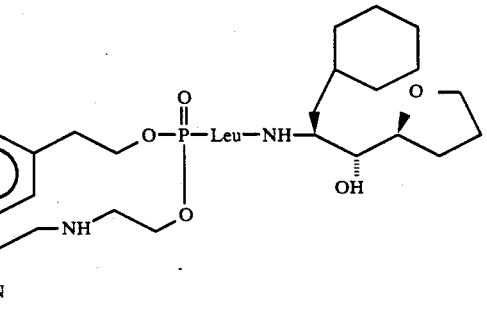 | $1.0 \times 10^{-7}$ |
| 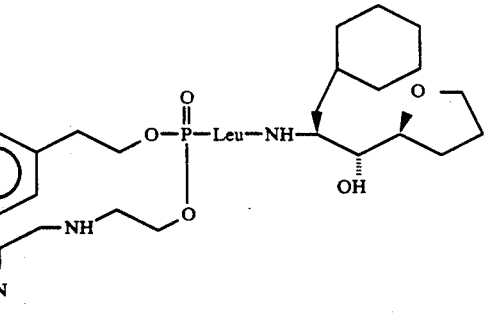 | $8.3 \times 10^{-8}$ |
| 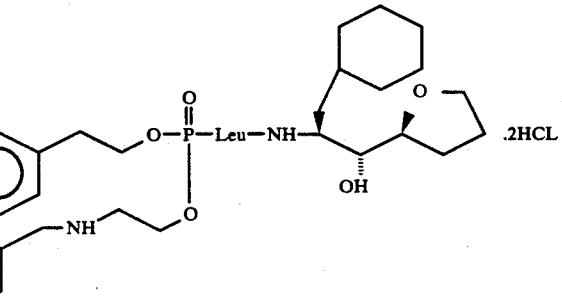 | $8.2 \times 10^{-8}$ |

TABLE I-continued

Renin Inhibitors

| Compound | IC$_{50}$ Molar Concentration |
|---|---|
| | $1.2 \times 10^{-7}$ |
| | $2.7 \times 10^{-7}$ |
| | $2.3 \times 10^{-7}$ |
| | $2.2 \times 10^{-7}$ |
| | $5.5 \times 10^{-8}$ |

TABLE I-continued

Renin Inhibitors

| Compound | $IC_{50}$ Molar Concentration |
|---|---|
| [structure: phenethyl-O-P(=O)(O-CH2-NH-pyridyl)-Leu-NH-CH(CH2-cyclohexyl)-CH(OH)-CH2-CH(tetrahydrofuran)] · 2HCL | $1 \times 10^{-7}$ |
| [structure: phenylpropyl-O-P(=O)(O-phenethyl)-Leu-NH-CH(CH2-cyclohexyl)-CH(OH)-CH2-CH(tetrahydrofuran)] | $1.6 \times 10^{-8}$ |
| [structure: phenylpropyl-O-P(=O)(O-CH2-protected sugar)-Leu-NH-CH(CH2-cyclohexyl)-CH(OH)-CH2-CH(tetrahydrofuran)] | $4.4 \times 10^{-9}$ |
| [structure: (Me2N-CH2CH2-O)(EtO)P(=O)-NH-CH(CH2-C6H4-OCH3)-C(=O)-NH-CH(iBu)-C(=O)-NH-CH(CH2-cyclohexyl)-CH(OH)-CH(tetrahydrofuran)] · Hcl | $3.3 \times 10^{-8}$ |
| [structure: (Br-CH2CH2-O)(EtO)P(=O)-NH-CH(CH2-C6H4-OCH3)-C(=O)-NH-CH(iBu)-C(=O)-NH-CH(CH2-cyclohexyl)-CH(OH)-CH(tetrahydrofuran)] | $5.2 \times 10^{-10}$ |

TABLE I-continued
Renin Inhibitors

| Compound | IC$_{50}$ Molar Concentration |
|---|---|
| i-BuO, Br-substituted phosphoramidate-Phe-Leu-NH-CH(CH$_2$-cyclohexyl)-CH(OH)-CH$_2$-(2-tetrahydrothienyl) | $7.1 \times 10^{-10}$ |
| i-BuO, morpholinoethyl phosphoramidate-Phe-Leu-NH-CH(CH$_2$-cyclohexyl)-CH(OH)-CH$_2$-(2-tetrahydrothienyl) | $3.5 \times 10^{-9}$ |
| (EtO)$_2$-P(O)-Phe-NH-CH(CH$_2$CO$_2$Bu)-C(O)-NH-CH(CH$_2$-cyclohexyl)-CH(OH)-(2-tetrahydrofuryl) | $3.1 \times 10^{-6}$ |
| (EtO)$_2$-P(O)-Phe-NH-CH(CH$_2$CO$_2$H)-C(O)-NH-CH(CH$_2$-cyclohexyl)-CH(OH)-(2-tetrahydrofuryl) | $1.0 \times 10^{-6}$ |

The novel compounds of the present invention have been found to be highly useful for lowering elevated blood pressure in mammals when administered in amounts ranging from about 5 mg to about 50 mg/kg of body weight per day.

The compounds of this invention are preferably administered by a parenteral route such as intravenous, intramuscular or subcutaneous, but may be administered orally if desired.

Compositions, according to the present invention, having the desired clarity, stability and adaptability for parenteral use are obtained by dissolving from 0.10% to 10% by weight of active compound in a vehicle consisting of a polyhydric aliphatic alcohol or mixtures of such alcohols. Especially satisfactory are glycerin, propylene glycol and polyethylene glycols. Although various mixtures of polyethylene glycols may be used, it is preferred to use a mixture having an average molecular weight of from about 200 to about 400.

In addition to the active compound, the parenteral solutions may also contain various preservatives to prevent bacterial and fungal contamination as well antioxidants to promote stability.

For intramuscular injection, the preferred concentration of active compound is 0.25 to 0.50 mg/ml of the finished compositions.

The novel compounds of this invention are equally adapted to intravenous administration when diluted with water or diluents employed in intravenous therapy such as isotonic glucose. For intravenous use, initial concentrations down to about 0.05 to 0.25 mg/ml of active compound are satisfactory.

The following specific examples illustrate the preparation of the compounds of this invention.

REFERENCE EXAMPLE 1

(S)-2-tert-Butoxycarbonylamino-4-methyl-(R,s)-1-(2-furanyl)pentan-1-ol

To 0.545 ml of furan in 10 ml of dry tetrahydrofuran under argon cooled to −20° C. is added 3.35 ml of 2.36M n-butyllithium in hexane. The solution is allowed to warm to 10° C. and stirred for 2 hours. The solution is chilled to −70° C. (dry ice-acetone) and 1.70 g of N-t-butoxycarbonyl-L-leucinal in 10 ml of tetrahydrofuran is added. After 1 hour at −70° C., 10 ml of 10% ammonium chloride is added. The mixture was concentrated under vacuum, diluted with water and extracted with ether. The combined ether extracts are dried and concentrated. The residue is purified twice by thick layer chromatography on silica gel plates to give 0.20 g of product as a gum; RF 0.22 on thin layer chromatography (silica gel) with hexane-ethyl acetate (4:1) as solvent.

REFERENCE EXAMPLE 2

(S)-2-Amino-3-cyclohexyl-(R)-1-(2-furanyl)propan-1-ol

A.

1,1-Dimethylethyl-(S)-[1-(cyclohexylmethyl)-2-(2-furanyl)-2-oxoethyl]carbamate.

A solution of 1.57 g of N-methoxy-N-methyl $N^\alpha$-t-butoxycarbonyl-L-cyclohexylalaninamide in 15 ml of dry tetrahydrofuran is cooled to −78° C. under argon. To the solution is added dropwise 5.9 ml of secondary butyllithium (0.85M in hexane). The viscous mixture is stirred at −78° C. for 1.5 hours and then warmed to 0° C. and stirred for 5 minutes. (Solution A)

A solution of 0.73 ml of furan in 5 ml of dry tetrahydrofuran is cooled to 0° C. and 3.8 ml of n-butyllithium (2.35M in hexane) added. The yellow suspension is stirred at 0° C. for 1.7 hours and then allowed to warm to room temperature for 15 minutes. (yellow solution B)

The yellow solution B is added to solution A and the mixture stirred at 0° C. for 1.5 hours. The mixture is quenched with 5 ml of saturated aqueous ammonium chloride and the solvent tetrahydrofuran removed under vacuum. The residue is diluted with 50 ml of ethyl acetate and 20 ml of 1N hydrochloric acid. The organic phase is separated and washed successively with 20 ml of saturated sodium bicarbonate, 20 ml of brine and dried over sodium sulfate. The solvent is removed under vacuum to give 1.63 g of a light brown gum. This gum is dissolved in ether-hexane (1:5 and the solution filtered through a thin pad of hydrous magnesium silicate. The pad is washed with ether-hexane (1:5) and the filtrate concentrated. The residue is triturated with hexane to give 1.23 g of light yellow crystals; $[\alpha]_D^{26} +41° \pm 1$ (c, 1.14, methanol). B. (S)-2-(N-tert-Butoxycarbonyl)amino-3-cyclohexyl(R,S)-1-(2-furanyl)propan-1-ol A solution of 0.16 g of 1,1-dimethylethyl (S)-[1-(cyclohexylmethyl)-2-(2-furanyl)-2-oxoethyl]carbamate in 2 ml of dry tetrahydrofuran and 0.2 ml of methanol is cooled to 0° C. under argon and 23 mg of sodium borohydride added. The solution is stirred at 0° C. for one hour and quenched with 2 ml of saturated aqueous ammonium chloride. The organic solvent is removed under vacuum and the residue diluted with 5 ml of saturated aqueous ammonium chloride. The organic solvent is removed under vacuum and the residue diluted with 5 ml of water and extracted with 10 ml of ethyl acetate. The organic layer is separated, washed successively with 5 ml of 0.5N hydrochloric acid, 5 ml of saturated sodium bicarbonate, 5 ml of brine and dried over sodium sulfate. The solvent is removed under vacuum to give 0.19 g of gummy solid. C. (4S-trans)-4-(Cyclohexylmethyl)-5-(2-furanyl)-2oxazolidinone To a solution of 0.23 g of (S)z-(N-tert-butoxycarbonyl)amino-3-cyclohexyl-(R,S)1-(2-furanyl)propan-1-ol in 3 ml of dichloromethane is added 0.06 ml of trifluoroacetic acid. The solution is stirred for 23 hours at room temperature, washed with 1N sodium hydroxide, dried over sodium sulfate and the solvent removed to give 0.17 g of solid. This solid is dissolved in dichloromethane-ethyl acetate (9:1) and filtered through a thin pad of hydrous magnesium silicate. The filter pad is washed with two 10 ml portions of dichloromethane-ethyl acetate (9:1) and the filtrate and washes combined. The solvent is removed and residual solid washed with hexane to give 0.10 g of white crystals; $[\alpha]_D^{26} -124° \pm 2$ (c,0.417, $CH_3OH$).

D.

(S)-2=Amino-3-cyclohexyl-(R)-1-(2-furanyl)propan-1-ol

A 0.15 g sample of (4S-trans)-4-(cyclohexylmethyl)-5-(2-furanyl)-2-oxazolidinone is dissolved in a mixture of 3 ml of ethanol and 3 ml of 1N sodium hydroxide. The solution is refluxed for 17 hours, diluted with 3 ml of water and concentrated under vacuum to remove the ethanol. The aqueous residue is extracted with two 5 ml portions of dichloromethane and the extracts dried over sodium sulfate. The solvent is removed to give 0.15 g of solid which is washed with hexane to give 0.13 g of white solid; $[\alpha]_D^{26} -10° \pm 2$ (c, 0.507, methanol).

REFERENCE EXAMPLE 3

N-(L-Leucyl)-(S)-2-amino-3-cyclohexyl-(R)1-(2-furanyl)propan-1-ol

To a solution of 1.4 g of imidazole in 18 ml of dichloromethane is added 0.90 ml of phenyl dichlorophosphate in 6 ml of dichloromethane. The mixture is stirred for 2o minutes, cooled to 0° C. and a solution of 0.60 g of imidazole, 1.60 g of $N^\alpha$-[(benzyloxy)carbon-yl]-L-leucine in 6 ml of tetrahydrofuran and 2.4 ml of N,N-dimethylformamide added. The mixture is stirred at 0° C. for 40 minutes and then 1.30 g of (S)2-amino-3-cyclohexyl-(R)-1-(2-furanyl)-propan-1-ol added. The mixture is stirred at 0° C. to 25° C. (ice bath allowed to melt) overnight and the solvent removed. The residue is dissolved in 20 ml of ethyl acetate and washed with water, 2N citric acid, sodium bicarbonate solution and dried ($MgSO_4$). The solution is filtered through a thin pad of hydrous magnesium silicate and the pad washed with several volumes of ethyl acetate. The filtrate is concentrated under vacuum to give 2.3 g of N-[N-(benzyloxy)carbonyl-L-leucyl]-(S)2-amino-3-cyclohexyl(R)1-(2-furanyl)propan-1-ol as an oil.

The preceding compound (1.85 g) and 1.0 g of ammonium formate in 24 ml of methanol under nitrogen is warmed on a steam bath and the solution is chilled to 0° C. To this mixture (without stirring) is added (by pipette) 0.96 g of 10% palladium on carbon suspended in 5 ml of ethanol. The mixture is stirred at 0° C. for 1 hour, diatomaceous earth added and the mixture filtered. The filter pad is washed with methanol and the filtrate evaporated to dryness. The residue is partitioned between ammonium hydroxide and dichloromethane. The organic layer is separated, dried ($MgSO_4$) and the solvent removed to give 1.24 g of a gum. Crystallization from 5 ml of diisopropyl ether gives 0.74 g of N-(L-leucyl)-(S)-2-amino-3-cyclo-hexyl-(R)-1-(2-furanyl)propan-1-ol as colorless crystals, mp 83°–84° C.

REFERENCE EXAMPLE 4

N-(L-Histidyl)-(S)-2-amino-3-cyclohexyl-(R)-1-(2-furanyl)propan-1-ol

To a mixture of 1.25 g of imidazole in 0.5 ml of dichloromethane is added 1.2 g of phenyl dichlorophosphate in 5 ml of dichloromethane. After stirring for 25 minutes the mixture is chilled to 0° C. and to the mixture is added a warm solution of 1.65 g of N$^\alpha$-(benzyloxyarbonyl)-L-histidine and 0.55 g of imidazole in 2 ml of dry N,N-dimethylformamide. The mixture was diluted to a volume of 10 ml the dichloromethane and stirred at 0° C. for one hour. To the mixture is added 1.25 g of (S)-2-amino-3-cyclohexyl-(R)-1-(2-furanyl)-propan-1-ol and the mixture stirred overnight at 0° C. to 25° C. (ice bath allowed to melt). The mixture is concentrated under vacuum and the residue in 20 ml of ethyl acetate washed with 5 ml of water, three 5 ml portions of 1M sodium bicarbonate and brine. The organic layer is dried (Na$_2$SO$_4$) and the solvent removed to give 2.4 g of N-[N-(benzyloxycarbonyl)-L-histidyl]-(S)-2-amino-3-cyclohexyl-(R)-1-(2-furanyl)propan-1-ol as a gum.

A mixture of the preceding gum (2.4 g), 1.52 g of ammonium formate, 0.37 ml of formic acid (90%) and 30 ml of methanol under nitrogen is chilled to 0° C. and then a slurry of 1.2 g of 10% palladium on carbon in ethanol is added by pipette. The cooled mixture is stirred 2.5 hours and filtered through diatomaceous earth. The filtrate is evaporated and to the residue is added one ml of concentrated ammonium hydroxide. The mixture is extracted successively with 10 ml, 5 ml and 5 ml portions of ethyl acetate. The combined extracts are dried (Na$_2$SO$_4$) and the solvent removed to give 1.2 g of a glass. This glass is chromatographed on a silica gel column with solvent dichloromethane-methanol-triethylamine (94:6:). Cuts containing product are combined, concentrated to dryness and partitioned between 10 ml of 2N ammonium hydroxide and 5 ml of dichloromethane. The organic layer is separated and the aqueous layer extracted with two 5 ml portions of dichloromethane. The organic layer and extracts are combined, dried (Na$_2$SO$_4$) and the solvent removed to give 0.22 g of solid; Mass spectrum (FAB): found, 361 (M+H); calc, 361(M+H).

REFERENCE EXAMPLE 5

(S)-2-Amino-4-methyl-(R)-1-(2-thienyl)pentan-1-ol

A 0.81 g of (S)-2-(tert-butoxycarbon-yl)amino-4-methyl-(R,S)-1-(2-thienyl)pentan-1-ol is dissolved in 5 ml of dichloromethane and 2.1 ml of trifluoroacetic acid added. This mixture is stirred for 3 hours, then poured with stirring into 15 ml of ice-cold 2N sodium hydroxide. The mixture is diluted with 25 ml of dichloromethane, the organic layer separated end the aqueous layer extracted with 20 ml of dichloromethane. The organic layer and extract are combined, washed with saturated sodium chloride solution, dried and the solvent removed in vacuo. The residue is chromatographed on a silica gel column with ethyl acetate:hexane (1:4),to give 0.72 g of (4S-trans)-4-(2-methylpropyl)-5-(2-thienyl)-2-oxazolidinone as a white solid $[\alpha]_D^{26} - 141°\pm2$ (c=0.570 methanol).

A 0.23 g portion of the above solid is dissolved in 5 ml of ethanol and 5 ml of 1N sodium hydroxide added. The solution is refluxed for 16 hours and then concentrated in vacuo. The residue is extracted with two 10 ml portions of dichloromethane. The extracts are combined, dried and the solvent removed in vacuo to give 0.2 g of the desired compound; Rf 0.45 [silica gel; ethyl acetate:hexane (1:2)].

REFERENCE EXAMPLE 6

(S)-2-Amino-3-cyclohexyl-(R)-1-(2-thienyl)propan-1-ol

To a solution of 1.57 g of N-methoxy-N-methyl N$^\alpha$-t-butoxycarbonyl-L-cyclohexylalaninimide in 10 ml of diethyl ether, cooled to −78° C., is added under argon 2.1 ml of 2.35M sec-butyllithium in hexane. After stirring for one hour, the mixture is allowed to warm to 0° C. To this is added a solution of 2-lithiothiophene in ether (prepared from 0.64 g of thiophene in 5 ml of ether and 3.2 ml of 3.25M n-butyllithium in hexane at 0° C. for one hour). This mixture is stirred at 0° C. for 2 hours, then quenched with 15 ml of 1N hydrochloric acid and diluted with 25 ml of ether. The organic layer is separated, washed successively with 15 ml of 1N hydrochloric acid, lo ml of water and 25 ml of saturated sodium bicarbonate, dried and filtered through a short pad of hydrous magnesium silicate. The filter pad is washed with ether, the filtrate and wash combined and evaporated in vacuo. The residue is washed with hexane and then chromatographed on 50 g of silica gel with ethyl acetate:hexane (1:20) as solvent to give 1.2 g of solid. Crystallization from hexane containing a trace of ether gave (S)-1,1-dimethylethyl [1-(cyclohexylmethyl)-2-oxo-2-(2-thienylethyl]carbamate as crystals; $[\alpha]_D^{26}$ +24°±1 (c=1.10, methanol).

A solution of 0.51 g of the above compound in 8 ml of dry tetrahydrofuran is cooled to −78° C. under argon and 3 ml of 1.0M potassium tri-sec-butylborohydride in tetrahydrofuran is added dropwise. This mixture is stirred at −78 ° C. for 4 hours, then quenched with 5 ml of saturated aqueous ammonium chloride, warmed to room temperature and the organic solvent removed in vacuo. The aqueous residue is diluted with 5 ml of water and 20 ml of ethyl acetate. The organic layer is separated and washed successively with two 5 ml portions of saturated aqueous ammonium chloride, 5 ml of saturated aqueous sodium bicarbonate and 5 ml of saturated aqueous sodium chloride solution, dried and the solvent removed in Vacuo to give (S)-2-(tertbutoxycarbonylamino)-3-cyclohexyl-(R,S)-1-(2-thienyl)propan-1-ol as a gum.

To an 18.4 g sample of the preceding gum in 330 ml of dichloromethane cooled to 0° C. is added 16.75 ml of trifluoroacetic acid. The solution is stirred overnight, cooled to 0° C. and ice cold 1N sodium hydroxide (approximately 300 ml) is added. The organic layer is separated and the aqueous layer extracted with two 350-ml portions of dichloromethane. The organic layer and extracts are combined, washed with two 250-ml portions of brine, dried (Na$_2$SO$_4$) and the solvent removed in vacuum to give 14.5 g of solid.

Trituration with 200 ml of hot hexane, cooling to room temperature and filtering gives 7.5 g of crystals of (4S-trans)-4-(cyclohexylmethyl)-5-(2-thienyl)-2-oxazolidinone as crystals, mp 105°–108° C.

A mixture of 7.0 g of the preceding compound in 13 ml of ethanol and 132 ml of 1N sodium hydroxide is refluxed for 17 hours. The solvent is removed under vacuum and the residue extracted twice with 200 ml of dichloromethane. The combined extracts are dried (Na$_2$SO$_4$) and the solvent removed under vacuum to give 4.64 g of crystals, mp 62°–64° C.; $[\alpha]_D^{26} -35°\pm1$ (c=1.145, CH$_3$OH).

REFERENCE EXAMPLE 7

N-(L-Histidyl)-(S)-2-amino-3-cyclohexyl-(R)-1-(2-thienyl)-propan-1-ol

A mixture of 1.18 g of N$^\alpha$-tert-butoxycarbonyl-L--histidine and 0.65 ml of triethylamine in 6 ml of chloroform is stirred and warmed on a steam bath until most of the solid dissolved. To this mixture is added 2.04 g of benzotriazol-1-yloxy-tris(dimethylamino)phosphonium hexafluorophosphate (BOP) in 2.5 ml of chloroform. The mixture is warmed on a steam bath for 3 minutes and 1.0 g of (S)-2-amino-3-cyclohexyl-(R)-1-(2-thienyl)-propen-1-ol added. The mixture is stirred at room temperature overnight and refluxed for 5 minutes. The solvent is removed under reduced pressure and the residue dissolved in 25 ml of ethyl acetate. The solution is washed with 10 ml of water, three 10 ml portions of 2M sodium carbonate and 10 ml of brine. The organic layer is dried ($Na_2SO_4$), the solvent removed and the residue dried under vacuum to give 1.7 g of N-[N-(tert-butoxycarbonyl)-L-histidyl]-(S)-2-amino-3-cyclohexyl-(R)-1-(2-thienyl)propan-1-ol as a white foam. To a 0.40 g sample of the preceding compound in one ml of tetrahydrofuran cooled to 0° C., is added 3 ml of ice-cold 4N hydrochloric acid. The resulting solution is chilled at 0° C. to 4° C. for seven days and filtered. To the filtrate is added 1.5 ml of 10N sodium hydroxide. The mixture is extracted twice with 2 ml of dichloromethane and the extract dried ($Na_2SO_4$). The solution is applied to two 20×20×0.2 cm silica gel plates and the plates developed with dichloromethanemethanol-ammonium hydroxide (9:1.2:02). The product band is removed and extracted with 5% concentrated ammonium hydroxide in methanol. The extract is concentrated under vacuum to give 0.22 g of the product of the Example as a gum.

REFERENCE EXAMPLE 8

2[[2-Amino-3-(1H-imidazol-4-yl)-1-oxopropyl]amino]-4,7-anhydro-1-cyclohexyl-1,2,5,6-tetradeoxy-L-arabino(and D-xylo)-Heptitol A mixture of 0.49 g of N-[N-(benzyloxycarbonyl)-L-histidyl]-(S)-2-amino-3-cyclohexyl-(R)-1-(2-furanyl)propan-1-ol and 0.68 g of ammonium formate in 6 ml of methanol is warmed to 60° C. and to the stirred mixture is added a suspension of 0.5 g of 10% palladium on carbon in 2.4 ml of ethanol. The mixture is stirred at 60° C. for 1.5 hour, diluted with 2 ml of Water and filtered through diatomaceous earth. The filter cake is washed with ethanol and the filtrate concentrated. The aqueous residue is diluted with 0.4 ml of concentrated ammonium hydroxide and extracted with ethyl acetate. The extract is dried ($Na_2SO_4$) and the solvent removed to give 0.33 g of solid. This solid is again subjected to hydrogenation with 0.5 g of 10% palladium on carbon, 0.68 g of ammonium formate in 6 ml of methanol at 60° C. for 1.5 hour. Work-up as previously described gives 0.28 g of solid.

REFERENCE EXAMPLE 9

(S)-2-tert-Butoxycarbonylamino-4-methyl-(R,S)-1-(2-thienyl)pentan-1-ol

To a solution of 1.4 g of thiophene in 20 ml of dry tetrahydrofuran under argon is added 7.05 ml of 2.36M n-butyllithium in tetrahydrofuran. The solution is stirred at room temperature for 45 minutes and then cooled to −70° C. (dry-ice acetone bath). A solution of 1.79 g of N-tert-butoxycarbonyl-L-leucinal in 10 ml of dry tetrahydrofuran is added via syringe. The mixture is stirred (−68° C.) for one hour and quenched with 10% ammonium chloride solution. After warming to room temperature, the solvent (tetrahydrofuran) is removed under vacuum. The residual aqueous mixture is extracted with ether. The combined ether extracts are washed with 50 ml of 1N hydrochloric acid, saturated sodium bicarbonate solution, saturated sodium chloride solution and dried. The solvent is removed and the residue chromatographed on a silica gel column with hexane-ethyl acetate (gradient elution) as solvent. The product is eluted with hexane-ethyl acetate (4:1). The fractions containing product are combined and the solvent removed under vacuum to give 1.15 g of gum; RF 0.34 on TLC (silica gel) with hexane-ethyl acetate (4:1).

REFERENCE EXAMPLE 10

N-(Diethoxyphosphinyl)-L-phenylalanine

A solution of 16.5 g of L-phenylalanine and 50 ml of triethylamine in 30 ml of water and 20 ml of ethanol under argon is chilled to 0° C. To this stirred solution is added dropwise a solution of diethyl phosphite (13.8 g) in 40 ml of carbon tetrachloride. After the addition, the mixture is stirred at room temperature for 3 hours and acidified with 3N hydrochloric acid (pH 2). The mixture is extracted with three 200-ml portions of ethyl acetate, the extract dried ($Na_2SO_4$) and the solvent removed under vacuum. The residue is dried under vacuum to give 23.5 g of an orange gum; $[\alpha]_D^{26} + 11° \pm 1$ (c=1.056, chloroform).

REFERENCE EXAMPLE 11

N-(Dibenzyloxyphosphinyl)-L-phenylalanine

A solution of 8.2 g of L-phenylalanine and 25 ml of triethylamine in 15 ml of water and 10 ml of ethanol under argon is chilled to 0° C. To this stirred solution is added dropwise 13.1 g of dibenzyl phosphite in 20 ml of carbon tetrachloride. After the addition, the mixture is stirred at room temperature for 3 hours and the mixture is concentrated under vacuum, diluted with ethyl acetate (100 ml), cooled to 0° C. and 50 ml of 3N hydrochloric acid added dropwise. The organic layer is separated and the aqueous layer extracted twice with 100 ml of ethyl acetate. The organic layer and extracts are combined, dried ($Na_2SO_4$) and the solvent removed. The residue is dried under vacuum to give 20.7 g of a yellow gum.

REFERENCE EXAMPLE 12

N-[N-(Dibenzyloxyphosphinyl)-L-phenylalanyl]-L-leucine

To a solution of 8.5 g of imidazole in 55 ml of dichloromethane under argon is added slowly a solution of 5.3 g of phenyl dichlorophosphate in 15 ml of dichloromethane. The suspension is stirred at room temperature for 0.5 hour, cooled to 0° C. and a solution of 10.62 g of N-(dibenzyloxyphosphinyl)-L-phenylalanine in 15 ml of dichloromethane added slowly. After stirring at 0° C. for one hour L-leucine methyl ester hydrochloride 4.5 g) is added in small portions. The mixture is stirred at 0° C. for 5 hours and allowed to warm to room temperature. The mixture is washed with 1N hydrochloric acid and the aqueous layer extracted with diohloromethane. The organic layer and extract are combined, washed with 0.5N hydrochloric acid, water, saturated sodium bicarbonate solution and dried ($Na_2SO_4$). The solvent is removed to give 11.2 g of a gum. Chromatography on silica gel with solvent ethyl acetate-hexane (1:1) followed by solvent ethyl acetate:hexane (2:1) gives 4.54 g of solid. Trituration with hexane (40 ml) gives 4.2 g of N-[N-(dibenzyloxyphosphinyl)-L-phenylalanyl]-L-leucine, methyl ester as crystals, mp 90°-92° C.; $[\alpha]_D^{26} - 17° \pm 1$ (c=1.059, methanol).

To the preceding compound (4.0 g) in 50 ml of methanol is added dropwise 14 ml of 1N sodium hydroxide and the mixture stirred 5 hours. An additional 7 ml of 1N sodium hydroxide is added and the mixture stirred at room temperature for 2.5 hours, chilled 2 days at 4° C. and concentrated under vacuum. The aqueous residue is extracted with ether (3 times with 20 ml), and the aqueous layer acidified with 2N hydrochloric acid and extracted with two 50 ml portions of dichloromethane. The extract is dried ($Na_2SO_4$) and the solvent removed to give 3.2 g of a white solid. Trituration with hexane gives 2.7 g of white crystals, mp 50°–53° C.;$[\alpha]_D^{26} -11° \pm$ (c=1.084, methanol).

REFERENCE EXAMPLE 13

(S)-N-[2-[(Diethoxyphosphinyl)oxy]-1-oxo-3-phenyl-propyl]-L-leucine

To a chilled (0° C.) solution of 0.35 g of L-3-phenyl-lactic acid in 4 ml of dry tetrahydrofuran is added 0.21 g of triphosgene and then 0.98 g of 1,8-bis(dimethylamino)naphthalene (proton sponge) in 2 ml of tetrahydrofuran is added. The resulting suspension is stirred in the dark at room temperature for 3 hours. To the mixture is added 0.42 g of methyl L-leucinate hydrochloride and 0.39 ml of triethylamine. The mixture is stirred at room temperature for 21 hours and filtered. The filter cake is washed with ethyl acetate. The filtrate is treated with 4 ml of 0.5N hydrochloric acid and concentrated under vacuum. The aqueous residue is diluted with 2 ml of 1N hydrochloric acid and extracted with 15 ml of ethyl acetate. The organic layer is separated and washed with 5 ml of 1N hydrochloric acid, 5 ml of saturated sodium bicarbonate and dried ($Na_2SO_4$). The solution is diluted with 15 ml of hexane and filtered through a pad of hydrous magnesium silicate (1.0 g). The filter pad is washed with two 5-ml portions of ethyl acetate-hexane (1:1) and the filtrate evaporated to give 0.44 g of white solid. This solid is washed with ethyl acetate-hexane (1:3) to give 0.42 g of methyl N-(2-hydroxy-1-oxo-3-phenylpropyl)-L-leucinate as a white solid. To a solution of the preceding compound (1.17 g) in 4 ml of dichloromethane is added 2.14 g of diethyl phosphorochloridate, 0.67 ml of triethylamine and 0.15 g of 4-(N,N-dimethylamino)pyridine. The mixture is stirred at room temperature under argon for 23 hours. An additional 0.71 g of diethyl phosphorochloridate and 0.12 g of triethylamine is added and the mixture stirred for an additional 18 hours. The mixture is treated with 20 ml of 10% sodium carbonate solution, stirred 15 minutes and the dichloromethane evaporated. The aqueous residue is extracted with 40 ml of ethyl acetate, the organic layer separate and washed with 20 ml 1N hydrochloric acid, sodium bicarbonate, brine and dried ($Na_2SO_4$). The solution is filtered through a thin pad of hydrous magnesium silicate, the pad washed with ethyl acetate and the filtrate evaporated. The residual solid (1.48 g) is chromatographed on silica gel With ethyl acetate-hexane (1:2) as solvent and then ethyl acetate-hexane (2:3) as solvent to give 1.10 g of colorless gum; $[\alpha]_D^{26} -32° \pm 1$ (c; 1.008, $CHCl_3$) to the preceding compound (0.43 g) in 2 ml of ethanol cooled to 0° C., is added 2 ml of 1N sodium hydroxide and the mixture stirred at 0° C. for 1.5 hour. A solution of 0.27 g of potassium bisulfate in 2 ml of water is added and the mixture concentrated under vacuum to remove the ethanol. The aqueous residue is diluted with 15 ml of ethyl acetate and 2 ml 0.5N hydrochloric acid. The organic layer is separated and washed with brine and dried ($Na_2SO_4$). The solvent is removed and the solid residue washed with hexane to give 0.47 g of colorless gum.

REFERENCE EXAMPLE 14

N-[N-(Diethoxyphosphinyl)-L-(4-methoxyphenyl)ala-nyl-L-leucyl]-(S)-2-amino-3-cyclohexyl-(R)-1-(2-furanyl)propan-1-ol To a stirred slurry of 0.88 g of L-(4-methoxyphenyl)alanine methyl ester hydrochloride in 40 ml of dichloromethane under argon is added 1.09 ml of triethylamine and 0.572 ml of diethyl phosphoryl chloride. The mixture is stirred overnight and then washed with 10% sodium bicarbonate solution and brine. The organic layer is concentrated under vacuum. The residue in ethyl acetate-dichloromethane (1:1) is filtered through a thin pad of hydrous magnesium silicate and the pad washed with ethyl acetate-dichloromethane (1:1) and the filtrate concentrated to dryness to an oil which crystallizes. The crystals are recrystallized from diisopropyl ether to give 0.932 g of methyl N-(diethoxyphosphinyl-L-(4-methoxy-phenyl)alanate as white crystals, mp 58.5°–60.5° C.; $[\alpha]_D^{26} -6° \pm 1$ (c=0.947, methanol).

To the preceding compound (0.179 g) in 10 ml of methanol is added 1.30 ml of 1M sodium hydroxide and the solution stirred for 1.5 hour. An additional 0.52 ml of 1M sodium hydroxide is added and after 45 minutes, 3N hydrochloric acid is added until the mixture is acidic and then the solvent is removed. The residue is extracted with dichloromethane. The extracts are dried ($MgSO_4$) and the solvent removed to give N-(diethoxyphosphinyl)-L-(4-methoxyphenyl)alanine as a gum.

This gum under argon is dissolved in 6 ml of dichloromethane and 52.3 mg of triethylamine and 0.229 g of benzotriazol-1-yloxytris(dimethylamino)phosphonium hexafluorophosphate (BOP). After stirring for one minute, 0.145 g of N-(L-leucyl)-(S)-2-amino-3-cyclohexyl-(R)-1-(2-furanyl)propan-1-ol is added and the mixture stirred overnight. The solvent is removed and the residue, dissolved in ethyl acetate, is washed with water. The organic layer is dried ($MgSO_4$) and the solvent removed. The residue is chromatographed on silica gel with solvent ethyl acetate-dichloromethane (1 1) to ethyl acetate (gradient elution) as eluent. The fractions containing product are combined and the solvent removed to give 0.170 g of a white foam; $[\alpha]_D^{26} -30° \pm 1$ (c=1.00, methanol).

Following the above procedure the following compounds may be prepared:

N-[N-(Dipropyloxyphosphinyl)-L-(4-methoxyphenyl)alanyl-L-leucyl]-(S)-2-amino-3-cyclohexyl-(R)-1-(2-furanyl)propan-1-ol N-[N-(Dipropylphosphinyl)-L-(3-(1'-naphthyl)alanyl-L-leucyl]-(S)-2-amino-3-cyclohexyl-(R)-1-(2-furanyl)propan-1-ol N-[N-(Disopropyloxyphosphinyl)-L-(4-methoxyphenyl)alanyl-L-leucyl]-(S)-2-amino-3-cyclohexyl-(R)-1-(2-furanyl)propan-1-ol N-[N-(Disopropyloxyphosphinyl)-L-3-(1'-naphthyl)alanyl-L-leucyl]-(S)-2-amino-3-cyclohexyl-(R)-1-(2-furanyl)propan-1-ol N-[N-(Diethoxyphosphinyl)-L-(4-methoxyphenyl)alanyl-L-histidyl]-(S)-2-amino-3-cyclohexyl-(R)-1-(2-furanyl)propan-1-ol

REFERENCE EXAMPLE 15

N-[N-(Diethoxyphosphinyl)-L-3-(1'-naphthyl)alanyl-L-leucyl]-(S)-2-amino-3-cyclohexyl-(R)-1-(2-furanyl)propan-1-ol A solution of 0.25 g of L-3-(1'-naphthyl)alanine in 5 ml of methanol is saturated with anhydrous hydrogen chloride gas at 0° C. and then stirred overnight. The solvent is removed under vacuum and methanol added and removed several times. The residue in diethyl ether is chilled and the precipitate filtered off to give 0.260 g of methyl L-3-(1'-naphthyl)alanate hydrochloride as a white solid; $[\alpha]_D^{26} +29° \pm 1$ (c=1,036, methanol).

To a slurry of the preceding compound (1.27 g) in 55 ml of dichloromethane under argon is added 1.46 ml of triethylamine and 0.763 g of diethyl phosphoryl chloride. The mixture is stirred at room temperature overnight and then washed with 10% sodium bicarbonate solution and brine. The solvent is removed, the residue dissolved in ethyl acetate-dichloromethane (1:1) and the solution filtered through a thin pad of hydrous magnesium silicate. The pad is washed with ethyl acetate-dichloromethane (1:1) and the filtrate concentrated to give 1.76 g of crystals. Recrystallization from diisopropyl ether gives 1.62 g of methyl N-(diethoxyphosphinyl)-L-3-(1'-naphthyl)alanate as white crystals, mp 110°-112° C.; $[\alpha]_D^{26} -23° \pm 1$ (c=1.093, methanol).

To the preceding compound (0.350 g) in 15 ml of methanol is added 2.88 ml of 1M sodium hydroxide and the mixture stirred for 2.5 hours at room temperature. Acid (3N HCl) is added until the mixture is acidic and the solvent removed. The residue is extracted with dichloromethane, the extracts dried (MgSO₄) and the solvent removed to give N-(diethylphosphinyl)-L-3-(1'-naphthyl)alanine.

The preceding compound (residue) is dissolved in 12 ml of dichloromethane under argon and 96.9 mg of triethylamine and 0.424 g of benzotriazol-1-yloxytris(dimethylamino)phosphonium hexafluorophosphate (BOP) added. After one minute 0.293 g of N-(L-leucyl)-(S)-2-amino-3-cyclohexyl-(R)-1-(2-furanyl)propan-1-ol is added and the mixture is stirred at room temperature overnight. The solvent is removed and the residue in ethyl acetate washed with 2M citric acid, 10% sodium bicarbonate, water and dried (MgSO₄). The solvent is removed to give 0.60 g of tan solid. This solid is dissolved in ethyl acetate and filtered through a pad of silica gel. The pad is washed with ethyl acetate and the filtrate evaporated to give 0.47 g of crystals; $[\alpha]_D^{26} -46° \pm 1$ (c=1.134, methanol); Mass spectrum (FAB): calc. 692.3441; Found: 692.3428.

REFERENCE EXAMPLE 16

N-[N-(Diethoxyphosphinyl)-L-phenylalanyl-L-leucyl](S)-2-amino-3-cyclohexyl-(R)-1-(2-furanyl)propan-1-ol N-[N-(Diethoxyphosphinyl)-L-phenylalanyl-L-leucine (0.62 g) is reacted with (S)-2-amino-3-cyclohexyl-(R)-1-(2-furanyl)propan-1-ol (0.22 g) to give 0.60 g of the product of the Example as a white solid; $[\alpha]_D^{26} -34° \pm 1$ (c=1.05, methanol).

REFERENCE EXAMPLE 17

N-[N-(Benzyloxy)carbonyl-L-leucyl]-(S) 2-amino-3-cyclohexyl-(R)-1-(2-furanyl)propan-1-ol To a solution of 4.0 g of N-(benzyloxy)carbonyl-L-leucine (4.99 g) in 40 ml of dry tetrahydrofuran is added 3.05 g of N,N-carbonyldiimidazole. The solution is stirred at room temperature for 2.0 hours and the 4.0 g of (S)-2-amino-3-cyclohexyl-(R)-1-(2-furanyl)propanol is added. After stirring 5 hours under argon, the solvent is removed and the residue is dissolved in 80 ml of dichloromethane. The solution is washed twice with 40 ml of 2N citric acid, once With 40 ml of water, 1N sodium bicarbonate and brine. The organic layer is dried (MgSO₄) and the solvent removed to give an oil. Crystallization from diisopropyl ether gives 7.0 g of white crystals, mp 95°-97° C.: $[\alpha]_D^{26} -39° \pm 1$ (c, 1.029, CH₃OH).

REFERENCE EXAMPLE 18

(S)-2-[(2-Amino-4-methyl-1-oxocentyl)amino]-4,7-anhydro-1-cyclohexyl-1,2,5,6-tetradeoxy-L-arabino-Heptitol and (S)-2-[(2-Amino-4-methyl-1-oxopentyl)amino]-4,7-anhydro-1-cyclohexyl-1,2,5,6-tetradeoxy-D-xylo-Heptitol N-[N-(benzyloxy)carbonyl-L-leucyl]-(S)-2-amino-3-cyclohexyl-(R)-1-(2-furanyl)propan-1-ol (7.0 g is dissolved in 80 ml of methanol under argon and 6.12 g of ammonium formate added. To this mixture under argon is added a suspension of (10%) palladium an carbon (3.17 g) in 10 ml of water. The suspension is added from a pipette and an additional 2 ml of water used as a rinse of the pipette. After the addition, the solution is stirred and the temperature rises from 22° C. to 30° C. After stirring for 1 hour, 5 ml of water and 3 g of diatomaceous earth is added and the mixture filtered through a pad of diatomaceous earth. The filter pad is washed with methanol and the filtrate concentrated under vacuum until solid begins to separate. The mixture is acidified with 120 ml of 2N citric acid and extracted with three 40-ml portions of ether. The aqueous layer is made basic with concentrated ammonium hydroxide and extracted with three 80-ml portions of diethyl ether. The extract is dried (Na₂SO₄) and the solvent removed to give 3.7 g of an oil. The preceding oil (4.27 g) is chromatographed with a Waters-prep 500 HPLC instrument (silica gel-two columns) with 1% triethylamine in ethyl acetate as solvent. Cuts containing the less polar component are combined, the solvent removed and the residue crystallized from diisopropyl ether to give 0.916 g of white crystals, mp 77°-78° C.; $[\alpha]_D^{26} -25° \pm 2$ (c, 0.421, CH₃OH)assigned D-xylo-diatereomer). Fractions containing the more polar component are combined the solvent removed and the residue crystallized from diisopropyl ether to give 1.23 g of white crystals, mp 90°-92° C., $[\alpha]_D^{26} -26° \pm 1$ (c, 1.067, CH₃OH)(assigned L-arabino-diastereomer).

REFERENCE EXAMPLE 19

(S)-2-[(2-Amino-4-methyl-1-oxopentyl)amino]-4,7-anhydro-1-cyclohexyl-1,2,5,6-tetradeoxy-L-arabino-Heptitol and (S)-2-[(2-Amino-4-methyl-1-oxopentyl)amino]-4,7-anhydro-1-cyclohexyl-1,2,5,6-tetradexoy-D-xylo-Heptitol Reduction of N-(L-leucyl)-(S)-2-amino-3-cyclohexyl-(R)-1-(2-furanyl)propan-1-ol with 10% palladium on carbon and ammonium formate as described in Reference Example 18 gives the products of the Example as a pair of diastereomers.

(a) white crystals, mp 77°-78° C., $[\alpha]_D^{26} -25°$ (c, 09.40, CH₃OH)(assigned D-xylo-diastereomer).

(a) white crystals, mp 90°-92° C.; [α $_D^{26}$ −26° (c, 1.0, CH$_3$OH) (assigned L-arabino-diastereomer).

REFERENCE EXAMPLE 20

2-Amino-4,7-anhydro-1-cyclohexyl-1,2,5,6-tetradeoxy-L-arabino-Heptitol and
2-Amino-4,7-anhydro-1-cyclohexyl-1,2,5,6-tetradexoy-D-xylo-Heptitol (S)-2-Amino-3-cyclohexyl-(R)-1-(2-furanyl)pro-pan-1-ol (4.5 g) is dissolved in 110 ml of methanol under argon and 5.1 g of ammonium formate added. To this mixture is added a suspension of 10% palladium on carbon (2.25 g) in 5 ml of water (without stirring mixture). The suspension is added from a pipette and an additional 1 ml of water used as a rinse of the pipette. After the addition, the mixture is stirred and the temperature rose to 30° C. The mixture is stirred 2 hours and filtered through diatomaceous earth. The filter pad is washed with methanol and the filtrate concentrated to dryness. To the residue is added 50 ml of 1N sodium hydroxide and the mixture extracted with dichloromethane. The extract is dried (Na$_2$SO$_4$) and the solvent removed to give 3.3 g of an oil. This oil (8 g) is chromatographed on silica gel with a waters-Prep 500 instrument with 2 % triethylamine in ethyl acetate as solvent. Fractions containing the first compound eluted are combined and the solvent removed to give a solid. Sublimation gives 0.42 g of crystals, mp 74°-76° C. assigned 2-amino-4,7-anhydro-1-cyclohexyl1,2,5,6-tetradeoxy-D-xylo-Heptitol structure. The later fractions from the column are combined and the solvent removed to give 0.39 g of a solid, mp 81°-82° C., assigned 2-amino-4,7-anhydro-1-cyclohexyl-1,2,5,6-tetradeoxy-L-arabino-Heptitol structure; [α]$_D^{26}$ −20°±1 (c, 1.082,CH$_3$OH).

REFERENCE EXAMPLE 21

2-[[2-Amino-3-(1H-imidazol-4-yl)-1-oxopropyl]amino]-4,7-anhydro-1-cyclohexyl-1,2,5,6-tetradeoxy-L-arabino-Heptitol To a mixture of 0.289 g of N$^\alpha$-(benzyloxycarbonyl)-L-histidine and 0.014 ml of triethylamine in 2 ml of N,N-dimethylformamide is added 0.44 g of benzotriazol-1-yloxytris(dimethylamino) phosphonium hexafluorophosphate (BOP). The mixture is stirred 1 minute and 0.200 g of 2-amino-4,7-anhydro-1-cyclohexyl-1,2,5,6-tetradeoxy-L-arabino-Heptitol added. The mixture is stirred overnight at room temperature and diluted with 5 ml of ethyl acetate. The mixture is washed three times with 1 ml of 2M sodium carbonate and with 1M citric acid-1M-sodium citrate buffer and brine. The organic layer is concentrated to give 0.35 g of a foam. Chromatography on silica gel with dichloromethane-methanol-ammonium hydroxide (9:1.2:0.2) gives 0.30 g of a glass. To the preceding glass (0.30 g) and 0.4 g of ammonium carbonate in 7 ml of methanol under nitrogen is added a slurry of 10% palladium on carbon in 1.5 ml of water. The mixture is stirred for 1.5 hour, filtered through diatomaceous earth and the filter pad washed with methanol. The filtrate is concentrated and the residue dissolved in 1 ml of methanol and 0.2 ml of concentrated ammonium hydroxide is extracted four times with 5 ml portions of chloroform. The extracts are combined, dried (Na$_2$SO$_4$) and the solvent removed to give 0.19 g of solid; [α]$_D^{26}$ −24°±1 (c, 1.003, CH$_3$OH).

REFERENCE EXAMPLE 22

N-[N(Benzyloxycarbonyl)-L-histidyl]-(S)-2-amino-3-cyclohexyl-(R)-1-(2-furanyl)propan-1-ol Imidazole (2.2 g) is dissolved in 26 ml of dichloroemthane and 2.06 g of phenyl dichlorophosphate in 8 ml of dichloromethane added. After stirring under argon for 10 minutes, the mixture is cooled to 0° C. and a solution of 2.82 g of N$^\alpha$-(benzyloxycarbonyl)-L-histidine 0.94 g of imidazole in a mixture of 3.4-ml of N,N-dimethylforamide and 17 ml of dichloromethane is added. The mixture is stirred at 0° C. for 1 hour and a solution of 2.14 g of (S)-2-amino-3-cyclohexyl-(R)-1-(2-furanyl)-propan-1-ol in 6 ml of dichloromethane added. The mixture is allowed to warm to room temperature over 5 hours and is stirred for 2 days. The mixture is concentrated under vacuum and diluted 100 ml of ethyl acetate. The mixture is washed 1M sodium bicarbonate, and a solution of 1M citric acid-1M-sodium citrate and dried (MgSO$_4$). The solvent is removed to give 4.8 g of solid. This solid is chromatographed on silica gel by HPLC on a Waters-Prep 500 A apparatus with ethyl acetate-methanol-triethylamine (96:2:2) as solvent. Cuts containing product are combined and the solvent removed under vacuum to give 2.54 g of solid; [α]$_D^{26}$ −21°±1 (c, 0.932, CH$_3$OH) FAB (Mass spectrum); found M+H=495.

REFERENCE EXAMPLE 23

2-[[2-Amino-3-(1H-imidazol-4-yl)-1-oxopropyl]-amino]-4,7-anhydro-1-cyclohexyl-1,2,5,6-tetradeoxy-L-arabino-Heptitol To a mixture of 0.289 g of N$^\alpha$-(benzyloxycarbonyl)-L-histidine and 0.014 ml of triethylamine in 2 ml of N,N-dimethylformamide is added 0.44 g of benzotriazol-1-yloxytris(dimethylamino) phosphonium hexafluorophosphate (BOP). The mixture is stirred 1 minute and 0.200 g of 2-amino-4,7-anhydro-1-cyclohexyl-1,2,5,6-tetradeoxy-L-arabino-Heptitol added. The mixture is stirred overnight at room temperature and diluted with 5 ml of ethyl acetate. The mixture is washed three times with 1 ml of 2M sodium carbonate and with 1M citric acid-1M-sodium citrate buffer and brine. The organic layer is concentrated to give 0.35 g of a foam. Chromatography on silic gel with dichloromethane-methanol-ammonium hydroxide (9:1.2:0.2) gives 0.30 g of a glass.

To the preceding glass (0.30 g) and 0.4 g of ammonium carbonate in 7 ml of methanol under nitrogen is added a slurry of 10% palladium on carbon in 1.5 ml of water. The mixture is stirred for 1.5 hour, filtered through diatomaceous earth and the filter pad washed with methanol. The filtrate is concentrated the residue in 1 ml of methanol and 0.2 ml of concentrated ammonium hydroxide is extracted four times with 5-ml portions of chloroform. The extracts are combined, dried (Na$_2$SO$_4$) and the solvent removed to give 0.19 g of solid; [α]$_D^{26}$ −24°±1 (c, 1.003, CH$_3$OH).

REFERENCE EXAMPLE 24

2-(Acetylamino)ethyl 3-phenylpropylphosphinate

To a solution of 0.31 g (1.5 mmol) of 1,3-dicyclohexylcarbodiimide in tetrahydrofuran (3 ml) is added 0.28 g (1.5 mmol) of 3-phenylpropylphosphinic acid in tetrahydrofuran (1 ml). The resulting suspension is stirred for 10 minutes at room temperature. N-acetyl ethanolamine (0.10 g, 1.0 mol) is then added, followed by 18 mg or 4-dimethylaminopyridine. The mixture is stirred for 2 hours. The solvent is evaporated under reduced pressure, and the residue is stirred with ethyl acetate (20 ml). The resulting suspension is filtered. The filtrate is washed with 5% potassium hydrogen sulfate (8 ml), saturated sodium bicarbonate (2×5 ml), and brine (5 ml), and evaporated to give 0.12 g of a colorless oil.

REFERENCE EXAMPLE 25

Methyl 3-phenylpropylphosphinate

Prepared in a similar manner as Reference Example 24 from 3-phenylpropylphosphinic acid and methanol to give a colorless oil.

REFERENCE EXAMPLE 26

2-(4-Morpholinyl)-2-oxoethyl 3-phenylpropylphosphinate

Prepared in a similar manner as Reference Example 24 using (4-morpholinocarbonyl)methanol in place of N-acetyl ethanolamine to give a white solid, mp 78°-80° C.

REFERENCE EXAMPLE 27

Phenyl phenylmethoxycarbonylamino chlorophosphate

A mixture of benzyl N-hydroxycarbamate (0.35 g, 2.1 mmol) and triethylamine (0.21 g, 2.1 mmol) in diethyl ether is cooled at 0° C. with stirring. To this is added a solution of phenyl dichlorophosphate (0.43 g, 2 mmol) in diethyl ether (1 ml). The resulting suspension is stirred at room temperature for 3 hours. It is then filtered and the solvents evaporated under reduced pressure to give 0.70 g of a colorless oil.

REFERENCE EXAMPLE 28

2-Methylpropylphenylmethyl chlorophosphate

To a solution of 0.54 g (5 mmol) of benzyl alcohol in diethyl ether (10 ml) is added 0.51 g (5 mmol) of triethylamine, followed by 0.96 g (5 mmol) of 2-methylpropyl dichlorophosphate with stirring and cooling at 0° C. The mixture is stirred at room temperature for 16 hours. The suspension is filtered and the solvents evaporated under reduced pressure to give 1.31 g of a colorless oil.

REFERENCE EXAMPLE 29

2-Methylpropyl dichlorophosphate

To a solution of 1.8 ml (20 mmol) of 2-methyl-1-propanol in diethyl ether (40 ml) is added 2.02 g (20 mmol) of triethylamine, followed by 1.9 ml (20 mmol) of phosphorus oxychloride with stirring and cooling at 0° C. The mixture is stirred at 0° C. for 1 hr. It is then filtered and evaporated under reduced pressure to give 3.86 g of a colorless oil.

REFERENCE EXAMPLE 30

4,7-Anhydro-2-(carboxyamino)-1,2,5,6-tetra deoxy-1-cyclohexyl-L-arabino(and D-xylo)-Heptitol, intramol.2,3-ester A solution of 50 mg (0.2 mmol) of (4S-trans)-4-(cyclohexylmethyl)-5-(2-furanyl)-2-oxazolidinone in ethyl acetate (4 ml) is hydrogenated at 25 psi, at room temperature, in the presence of 80 mg. of 5% Rhodium on alumina for 4 hours. The mixture is then filtered through Celite and the filter pad is washed with 6 ml of ethyl acetate. The filtrate is washed with 5 ml of 1N hydrochloric acid and 5 ml of brine, dried over anhydrous sodium sulfate, and evaporated. The residue is triturated with a small amount of hexane to give 45 mg of a white solid (a mixture of two diastereomers in about 1:1 ratio). A 10 g sample is hydrogenated in a similar manner to give 7.5 g of white solid. Chromatography of 8.5 g on silica gel by HPLC on a Waters Prep 500 instrument with hexane-ethyl acetate (3:1) as solvent give 4.05 g of L-arabino diasteromer as white crystals, mp 93°-96° C. and 2.3 g of D-xylo diasteromer as white crystals, mp 143°-145° C.

REFERENCE EXAMPLE 31

2-Amino-4,7-anhydro-1-cyclohexyl-1,2,5,6-tetradeoxy-L-arabino-Heptitol

To a solution of 0.70 g of 4,7-anhydro-2-(carboxyamino-1-cyclohexyl-1,2,5,6-tetradeoxy-L-arabino-Heptitol, intramol. 2,3-ester in ethanol (14 ml) is added with stirring, 14 ml of 1N sodium hydroxide. The mixture is heated at 70° C. for 16 hours. The ethanol is evaporated and the aqueous residue is extracted with 3×100 ml of methylene chloride. The combined extracts are dried over anhydrous sodium sulfate, and evaporated to give 0.63 g of a white solid, $[\alpha]_D^{26} -19° -1$ (c, 1.089, MeOH).

REFERENCE EXAMPLE 32

N-Methoxy-N-methyl $N^\alpha$t-butoxycarbonyl-L-phenylalaninamide

To a solution of 44.2 g (0.65 mole) of imidazole in methylene chloride (300 ml) is added with stirring 19.4 ml (0.13 mole of phenyldichlorophosphate. The mixture is stirred at room temperature for 0.5 hour, and then cooled to 0° C. A solution of 34.5 g (0.13 mole) of N-t-butoxycarbonyl-L-phenylalamine in methylene chloride (120 ml) is added, and the mixture is stirred at 0° C. for 1 hour. N,O-Dimethylhydroxylamine hydrochloride (15.2 g, 0.156 mole) is then added in small portions. The resulting mixture is stirred at 0° C. for 5 hours and at room temperature for 16 hours. The final suspension is diluted with 400 ml of methylene chloride, washed with 1N hydrochloric acid (2×200 ml), water (200 ml), saturated potassium carbonate solution (200 ml), and brine (200 ml), and dried over anhydrous magnesium sulfate. Removal of solvents gives 40.2 g of a pale yellow oil, $[\alpha]_D^{26} +22° ±1$ (c, 1.052, CHCl$_3$).

REFERENCE EXAMPLE 33

1,1-Dimethylethyl-(S)-[1-phenyl-2-(2-furanyl)-2-oxoethyl]carbamate

Prepared in a similar manner as Reference Example 2(A), using N-methoxy-N-methyl $N^\alpha$-t-butoxycarbonyl-L-phenylalaminamide as starting material. $[\alpha]_D^{26} +70° ±1$ (c, 1.024, MeOH).

REFERENCE EXAMPLE 34

(S)-2-(N-t-Butoxycarbonyl)amino-3-phenyl-(R,S)-1-(2-furanyl)propan-1-ol

Prepared in a similar manner as Reference Example 2(B), using 1,1-dimethylethyl-(S)-[1-phenyl-2-(2-furanyl)-2-oxoethyl]carbamate as starting material. $[\alpha]_D^{26} -24° ±1$ (c, 1.152,MeOH).

REFERENCE EXAMPLE 35

(4S-trans)-4-Phenyl-5-(2-furanyl)-2-oxazolidinone

Prepared in a similar manner as Reference Example 2(C), using (S)-2-(N-t-butoxycarbonyl)amino-3-phenyl-(R,s)-1-(2-furanyl)propan-1-ol as starting material. $[\alpha]_D^{26} -122° \pm 1$ (c, 1.003, MeOH).

REFERENCE EXAMPLE 36

4,7-Anhydro-2-(carboxyamino)-1,2,5,6-tetradeoxy-1-phenyl-L-arabino(and D-xylo)-Heptitol intramol. 2,3-ester A solution of 4.0 g (16 mmol) of (4S-trans)-4-phenyl-5-(2-furanyl)-2-oxazolidinone is hydrogenated at 30 psi, in the presence of 1.0 g of 5% Rhodium on alumina, for 6 hours. The mixture is filtered through Celite, and the filter pad dluted with 20 ml of ethyl acetate. The filtrate is washed with 2×15 ml of 1N hydrochloric acid, and 15 ml of brine, dried over anhydrous sodium sulfate, and evaporated to give 3.02 g of a beige solid. The crude solid is chromatographed with silica gel (230–400 mesh), and ethyl acetate-methylene chloride (1:5) as the eluting solvent, yielding:

A. 1.41 g of 4,7-anhydro-2-(carboxyamino)-1,2,5,6-tetradeoxy-1-phenyl-L-arabino-Heptitol intramol. 2,3-ester as a white solid, $[\alpha]_D^{26} -62° \pm 1$ (c, 1.010, CHCl$_3$).

B. 0.90 g of 4,7-anhydro-2-(carboxyamino)-1,2,5,6-tetradeoxy-1-phenyl-D-xylo-Heptitol intramol. 2,3-ester as white needles,.$[\alpha]_D^{26} -107° \pm 1$ (c, 0.986, CHCl$_3$).

REFERENCE EXAMPLE 37

4,7-Anhydro-2-(carboxyamino)-1,2,5,6-tetradeoxy-1-cyclohexyl-L-arabino-Heptitol intramol. 2,3-ester A mixture of 0.74 g (3 mmol) of Reference Example 36(A) and 0.30 g of 5% Rhodium on alumina in methanol (30 ml) is hydrogenated at 25 psi for 4 hours. The mixture is filtered through diatomaceous earth and the filtrate is evaporated. The residue is triturated with hexanes to give 0.76 g of a white solid, $[\alpha]_D^{26} -73° \pm 1$ (c, 0.98,MeOH).

REFERENCE EXAMPLE 38

1,2,4,5,6,7-Hexadeoxy-2-[[(1,1-dimethylethoxy) carbonyl]amino]-4,7-epithio-1-phenyl-L-arabino (and D-xylo)-Heptitol, S-oxide To a solution of 35.1 ml of dry diisopropylamine in 100 ml of tetrahydrofuran chilled in an ice bath, under argon is added dropwise, 100 ml of n-butyllithium (2.4 molar) in hexane via syringe over 1 hour. To this solution is added dropwise 26.0 g of tetramethylene sulfoxide and the solution allowed to warm to room temperature (Solution A).

To a mixture of 13.3 g of N-tert-butoxycarbon-yl-L-phenylalanine and 8.1 g of N,N-carbonyldiimidazole is added 100 ml of dry tetrahydrofuran. The mixture is stirred under argon until gas evolution ceased and for an additional 15 minutes (yellow solution B). The solution B is added in four separated portions via syringe to the stirred Solution A at room temperature. The mixture is stirred for 16 hours at room temperature and is quenched with 75 ml of saturated ammonium chloride solution. The mixture is filtered and the filtrate extracted with ethyl acetate and dichloromethane. The combined extracts are washed with saturated sodium chloride solution, dried (Na$_2$SO$_4$) and the solvent removed. The residue (24.4 g) is chromatographed on silica gel with a Waters-Prep 500 HPLC apparatus with ethyl acetate as solvent. Cuts containing product are combined and the solvent removed to give 5.15 of 1,1-dimethylethyl[R-(R*,S*) and S-(R*,R*,)]-[2-oxo-1-(phenylmethyl)-2-(tetrahydro-2-thienyl)ethyl]carbamate, S-oxide as a gum. $[\alpha]_D^{26} -5° \pm 1$ (c, 1.075, CH$_3$OH); mass spectrum (CI) (MN+ =352). Reduction of 0.20 g samples of the preceding compound with diisobutylaluminum hydride in tetrahydrofuran or lithium aluminum hydride in tetrahydrofuran or sodium borohydride in ethanol give a gum as a mixture of diasteromers. The products of the Example are separated by chromatography on silica gel with a Waters-Prep 500 apparatus with a mixture of ethyl acetate-hexane as solvent.

REFERENCE EXAMPLE 39

1,1-Dimethylethyl [1-(cyclohexylmethyl)-2-hydroxy-2-(tetrahydro-2H-pyran-2-yl)ethyl]-carbamate A solution of 1.582 g of 2-(phenylsulfonyl)-tetrahydropyran in 20 ml of tetrahydrofuran is cooled in a dry ice acetone bath and 4.7 ml of a solution of n-butyllithium in hexane (1.5M) is added. After stirring for 15 minutes 0.638 g of N-tert-butylcarbonyl-L-3-(cyclohexyl)alanal in 5 ml of tetrahydrofuran is added and the mixture stirred at −78° C. for 15 minutes. The mixture is allowed to warm to 0° C. over a period of 2 hours and a solution of 25 ml of saturated sodium bicarbonate is added. The mixture is extracted with two 100 ml portions of ether, the extract washed with saturated sodium chloride solution, dried (Na$_2$SO$_4$) and the solvent removed under vacuum to give 1.30 g of 1,1-dimethylethyl [1-(cyclohexylmethyl)-2-(5,6-dihydro-4H-pyran-2-yl)-2-hydroxyethyl]-carbamate as a light yellow oil. a 1.13 g sample of the preceding compound is dissolved in 10 ml of methanol and 0.66 g of ammonium formate added. To the mixture under argon is added a slurry of 0.39 g of 10% palladium on carbon in 5 ml of water. The mixture is stirred for 6 hours and filtered through diatomaceous earth. The filter pad is washed with methanol and the filtrate concentrated under vacuum. The mixture is extracted with two 50-ml portions of ethyl acetate and the extract washed with saturated sodium chloride solution. The organic layer is dried (Na$_2$SO$_4$) and the solvent removed under vacuum to give a pale yellow gum.

REFERENCE EXAMPLE 40

1-Cyclohexyl-1,2,4,5,6,7-hexadeoxy-2-[[(1,1-dimethylethoxy)carbonyl]amino]-4,7-epithio-L-arabino (and D-xylo)-Heptitol, S-oxide To a solution of 15.6 ml of diisopropylamine in 50 ml of dry tetrahydrofuran under argon is cooled in an ice-methanol bath and 0.46 ml of n-butyllithium in hexane (2.5M) is added slowly. To this solution cooled at 0° C. is added 10.4 ml of tetramethylenesulfoxide and then the mixture is allowed to warm to 25° C. (Mixture A).

A solution of 6.25 g of N-tert-butoxycarbonyl-L-phenylalamine and 3.72 g of N,N-carbonyldiimidazole in 50 ml of tetrahydrofuran is stirred under argon at room temperature for 0.5 hour and refluxed for 0.5 hour and then chilled. (Solution B).

The solution B is added over 15 minutes via double needle technique under nitrogen to the mixture A while cooling. The mixture is stirred for 3 hours and quenched with 50 ml of saturated aqueous ammonium chloride and 100 ml of ethyl acetate added. The organic layer is separated and washed with 1M sodium bicarbonate solution, 2M aqueous citric acid solution and 50 ml of brine. The organic layer is dried (Na$_2$SO$_4$) and the solvent removed to give 8 g of yellow oil. This oil is chromatographed on silica gel by HPLC on a Waters-Prep 500 apparatus with hexane-ethyl acetate (9:1) as solvent. The major broad fraction containing two major components by thin layer chromatography (silica gel with 9:1 hexane-ethyl acetate) is collected and the solvent removed to give 1,1-dimethylethyl [R,-(R*,S*) and S-(R*, R*)]-[2-oxo-1-(cyclohexylmethyl)-2-(tetrahydro-2-thienyl)ethyl]-carbamate, S-oxide as a gum: $[\alpha]_D^{26} -11°\pm1$ (c, 0.774, CH$_3$OH).

The preceding compound (0.5 g) is dissolved in 5 ml tetrahydrofuran and added to a mixture of sodium borohydride in 5 ml of tetrahydrofuran cooled to −78° C. The mixture is stirred 2 hours at −78° C. and 2 hours at room temperature and quenched with aqueous ammonium chloride. The mixture is concentrated, extracted with ethyl acetate and the extract dried (Na$_2$SO$_4$). The solvent is removed to give a gum.

REFERENCE EXAMPLE 41

2-[[2-Amino-3-(1H-imidazol-4-yl)-1-oxopropyl]amino]-4,7-anhydro-1-cyclohexyl-1,2,5,6-tetradeoxy-L-arabino-(and D-xylo)-Heptitol (1:1 mixture of diastereomers)

To a mixture of 6.65 g of N$^\alpha$-benzyloxycarbonyl-L-histidine in 45 ml of dry N,N-dimethylformamide under nitrogen is added 0.32 ml of triethylamine. To the mixture is added 11.1 g of benzotriazol-1-yloxytris(dimethylamino)phosphonium hexafluorophosphate (BOP). After 1 minutes 4.54 g of a mixture of 2-amino-4,7-anhydro-1-cyclohexyl-1,2,5,6-tetradeoxy-L-arabino(and D-xylo)-Heptitol (1:1 mixture of diastereomers) in 5 ml of N,N-dimethylformamide is added. The mixture is stirred at room temperature for 2 days and then concentrated under vacuum. The residue is dissolved in 100 ml of ethyl acetate and the solution washed with 1M sodium carbonate, 1M citric acid-1M-sodium citrate buffer, brine and dried (Na$_2$SO$_4$). The filtrate is concentrated under vacuum. The residue is chromatographed on silica gel by HPLC with a Waters-Prep 500 instrument with ethyl acetate-methanol (4:1) containing 2% triethylamine. The combined product fractions are concentrated under vacuum to give 7.3 g of solid.

To a sample (7.18 g) of the preceding compound and 9.1 g of ammonium formate in 160 ml of methanol under argon is added (without stirring) a suspension of 3.7 g of 10% palladium on carbon in 35 ml of water. The mixture is stirred (without cooling) for 1 hour. Diatomaceous earth which had been washed with water is added and the mixture filtered through diatomaceous earth. The filter pad is washed with methanol and the filtrate concentrated. The aqueous residue is made basic with concentrated ammonium hydroxide and extracted with ethyl acetate. The extract is dried (Na$_2$SO$_4$) and the solvent removed to give 3.85 g of a glass (90% pure by pmr analysis): $[\alpha]_D^{26} -20°\pm1$ (c, 1.06, CH$_3$OH).

REFERENCE EXAMPLE 42

(S)2-Amino-3-cyclohexyl-(R)1-(5-acetyl-2-furanyl)propan-1-ol

To a solution of 0.50 g of (4S-trans)4-(cyclohexylmethyl)-5-(2-furanyl)-2-oxazolidinone in 8 ml of tetrahydrofuran, cooled to −78° C., was added 1.8 ml of n-butyllithium in hexane (2.2M). After 15 minutes the solution was warmed to room temperature and N-methoxy-N-methyl acetamide in 1 ml of tetrahydrofuran was added. The mixture was stirred at room temperature for 3 hours and quenched with 4 ml of saturated ammonium chloride solution and 4 ml of water. The mixture was concentrated under vacuum to remove the tetrahydrofuran and then extracted with 20 ml of ethyl acetate. The extract was washed with 10 ml each of 1N hydrochloric acid, saturated sodium bicarbonate and brine. The organic layer was dried (Na$_2$SO$_4$) and the solvent removed to give 0.58 g of solid. Flash chromatography on silica gel with ethyl acetate-hexane (1:1) as solvent gave 0.29 g of (4S-trans)4-(cyclohexylmethyl)-5-(5-acetyl-2-furan-yl)-2-oxazolidinone as a cream colored solid; $[\alpha]_D^{26} -116°\pm1$ (c, 0.773, CH$_3$OH).

The preceding compound was dissolved in a mixture of 4 ml of ethanol and 4 ml of 1N sodium hydroxide and the solution heated at 80° C. for 6 hours. The solution was diluted with 4 ml of water, concentrated to remove the ethanol, and extracted twice with 8 ml of dichloromethane. The extract was dried (Na$_2$SO$_4$) and the solvent removed to give 0.11 g of solid. Flash chromatography on silica gel with 10% methanol in dichloromethane gave 85 mg of product as a yellow solid: $[\alpha]_D^{26} +64°\pm2$ (c, 0.464, CH$_3$OH). The following Reference Examples may be prepared by the foregoing procedures of Reference Example 42.

(S)2-amino-3-cyclohexyl-(R)1-(5-acetyl-2-thienyl)propan-1-ol (S)2-amino-3-cyclohexyl-(R)1-(5-propionyl-2-furanyl)-propan-1-ol (S)2-amino-3-cyclohexyl-(R)1-(5-propionyl-2-thienyl)-propan-1-ol

REFERENCE EXAMPLE 43

(3-Phenylpropyl)phosphinic acid, ester with 1,2:3,4-bis-O-(methylethylidene)-alpha-D-galactopyranose Prepared in a similar manner as Reference Example 24, from 3-phenylpropylphosphinic acid and 1,2:3,4-di-O-isopropylidene-D-galactopyranose.

REFERENCE EXAMPLE 44

2-Phenylethyl 3-(phenylpropyl)phosphinate

Prepared in a similar manner as reference example 24, from 3-phenylpropylphosphinic acid and phenethyl alcohol.

REFERENCE EXAMPLE 45

Bis-(2-phenylethyl)chlorophosphate

To a solution of phosphorus oxychloride ((1.53 g, 10 mmol) in anhydrous diethyl ether (20 ml), cooled at 0° C. under argon, is added a solution of 2.44 g (20 mmol) of phenethyl alcohol in diethyl ether (5 ml), followed by 2.02 g (20 mmol) of triethylamine in diethyl ether (5 ml). The mixture is stirred for 1 hour at 0° C., and then for 17 hours at room temperature. The final suspension is filtered, and the filtrate is evaporated to give 3.07 g of a colorless liquid.

REFERENCE EXAMPLE 46

2-Bromoethyl 2-phenylethylchlorophosphate

To a solution of 0.77 g (5 mmol) of phosphorus oxychloride in anhydrous diethyl ether (10 ml), cooled at 0°

C. under argon, is added 0.61 g (5 mmol) of phenethyl alcohol in diethyl ether (1 ml) with constant stirring. A solution of 0.51 g (5.1 mmol) of triethylamine in diethylether (1 ml) is added slowly, and the resulting suspension is stirred at 0° C. for 1 hour. The mixture is then treated with a solution of 2-bromoethanol (0.66 g, 5 mmol) in diethylether (1 ml), followed by 0.50 g (5 mmol) of triethylamine in diethylether (1 ml). Stirring is continued for 21 hours at room temperature. The final suspension is filtered, and the filtrate is evaporated in vacuo to give 1.54 g of colorless oil.

REFERENCE EXAMPLE 47

3-Bromopropyl 2-phenylethyl chlorophosphate

Prepared in a similar manner as Reference Example 46, from 3-bromopropanol.

REFERENCE EXAMPLE 48

N-(diisobutoxyphosphinyl)-L-phenylalanine

Prepared in a similar manner as Reference Example 11, using diisobutyl phosphite as the reagent.

REFERENCE EXAMPLE 49

N-[N-(Diisobutoxyphosphinyl)-L-phenylalanyl]-L-leucine

Prepared in a similar manner as Reference Example 12 from N-(diisobutoxyphosphinyl)-L-phenylalanine (Reference Example 48).

REFERENCE EXAMPLE 50

N-[(2-phenylethoxy) (3-phenylpropyl)phosphinyl]-L-leucine

To a solution of 9.6 g of 2-phenylethyl 3-(phenylpropyl)phosphinate in 18.6 ml of carbon tetrachloride under argon is added slowly 18.6 ml of triethylamine. After stirring for 15 minutes, a mixture of methyl L-leucinate, hydrochloride in 30 ml of dichloromethane is added. The mixture is stirred at room temperature for 3.25 hours and the solvent removed under vacuum. To the residue is added 150 ml of ethyl acetate and the mixture is washed with 1N hydrochloric acid (2×60 ml), 1N sodium hydroxide (2×60ml) and brine(60 ml). The organic layer is dried (Na$_2$SO$_4$) and the solvent removed under vacuum. The residue 10 g is purified by chromatography on silica gel (2 columns) by HPLC with a Waters-Prep 500 instrument with hexane-ethyl acetate (1:1) as solvent to give 3.40 g of N-[(2-phenylethoxy) (3-phenylpropyl)phosphinyl-L-leucine, methyl ester as a gum; $[\alpha]_D^{26} -7° \pm 1$ (c,1.00, CHCl$_3$) to a solution of 3.32 of the preceding compound in 28.5 ml of methanol is added 11.4 ml of 1N NaOH. The mixture is stirred for 1 hour and 1.9 ml of 1N NaOH added. After 3 hours, 2 ml of 1N NaOH is added and the mixture stirred for an additional 1.5 hour and diluted with 20 ml of water. The solution is concentrated to remove the methanol and then extracted with ether (2×20 ml). The aqueous solution is acidified with 1N HCl(30 ml) and extracted with ethyl acetate (2×40 ml). The extract is dried (Na$_2$SO$_4$) and the solvent removed to give 3.12 g of colorless gum.

REFERENCE EXAMPLE 51

2-Amino-1-cyclohexyl-1,2,4,5,6,7-hexadeoxy-4,7-epithio-L-arabino-Heptitol to a solution of 0.1 g of 4,7-anhydro-2-carboxyamino)-1-cyclohexyl-1,2,5,6-tetradeoxy-D-xylo-Heptitol in 1 ml of dichloromethane is added 1 ml of 1M borontribromide in dichloromethane. The mixture is stirred at room temperature for 16 hours, water (2 ml) is added and the dichloromethane allowed to evaporate. The mixture is filtered to give 0.114 g of crystals, mp. 117°-121° C. Recrystallization from dichloromethanediisopropyl ether gives 0.094 g of [4S-[4α,5β(S*)]]-5-(4-bromo-1-hydroxybutyl)-4-(cyclo-hex-ylmethyl)-2-oxazolidinone as needles, mp. 124°-125° C.; $[\alpha]_D^{26} -64° \pm 1$(c, 1.018, CH$_3$OH).

The preceding compound (0.222 g) and 0.103 g of potassium thioacetate in 2 ml of acetonitrile is stirred overnight. The mixture is diluted with 10 ml of water and filtered to give 0.193 g of crystals, mp. 107°-108° C. Recrystallization from dichloromethanediisopropyl ether gives 2-(carboxyamino)-1-cyclohexyl-1,2,5,6-tetradeoxy-7-thio-D-xylo-Heptitol, 7-acetate, intramol. 2,3-ester as crystals, mp. 108°-109° C.; $[\alpha]_D^{26} -60° \pm 1$ (c, 1.00, CH$_3$OH).

To the preceding compound (2.85 g) in 16 ml of dichloromethane (cooled to 0° C.) is added 1.8 ml of dry triethylamine and 1.0 ml of methanesulfonyl chloride. The mixture is stirred for one hour diluted with 40 ml of dichloromethane and 16 ml of water. The organic layer is separated and the aqueous layer extracted with dichloromethane. The organic layer and extracts are combined, dried and the solvent removed to give 3.6 g of crystals, mp. 143°-153° C. Recrystallization from diisopropyl ether gives 0.41 g of 2-(carboxyamino)-1-cyclohexyl-1,2,5,6-tetradeoxy-7-thio-D-xylo-Heptitol,7-acetate, 4-methanesulfonate, intramol. 2,3-ester as crystals, mp. 163°-164° C.; $[\alpha]_D^{26} -45° \pm 1$(c, 1.0, CHCl$_3$).

Anal. Calc. for C$_{17}$H$_{29}$NO$_6$S$_2$: C, 50.1; H, 7.2; N, 3.4; S, 15.7 Found: C, 49.6; H, 7.1; N, 3.0; S, 15.1.

The preceding compound (42 mg) in 0.8 ml of dichloromethane and 0.2 ml of methanol is added 0.048 g of cesium carbonate. After 2 hours, water (0.7 ml) is added and the organic layer separated. The aqueous layer is extracted with dichloromethane and the organic layer and extracts combined. The extract is dried (MgSO$_4$) and the solvent removed to give 25 mg of 2-(carboxyamino)-1-cyclohexyl-1,2,4,5,6,7-hexadeoxy-4,7-epithio-L-arabino-Heptitol, intramol. 2,3-ester as crystals, mp. 118°-119° C. A solution of the preceding compound (0.23 g) and 4.2 ml of 1N sodium hydroxide in 4.2 ml of ethanol is refluxed overnight. The solution is concentrated to ½ volume and the oil which separates crystallized. The aqueous layer is extracted with dichloromethane and the organic layer separated and the solvent removed to give crystals. The two batches of crystals are combined and sublimed to give 0.115 g of 2-amino-1-cyclohexyl-1,2,4,5,6,7-hexadeoxy-4,7-epithio-L-arabino-Heptitol as crystals, mp. 58°-59° C.; $[\alpha]_D^{26} +50° \pm 1$(c, 1.00, CH$_3$OH).

REFERENCE EXAMPLE 52

2-Amino-1-cyclohexyl-1,2,4,5,6,7-hexadeoxy-4,7-epithio-L-arabino-Heptitol, S-oxide To a solution of 0.24 g of 2-amino-1-cyclohexyl-1,2,4,5,6,7-hexadeoxy-4,7-epithio-L-arabino-Heptitol in 2 ml of dichloromethane is added 0.26 g of 3-chloroperbenzoic acid. After 10 minutes the solution is washed three times with 2 ml of 2M potassium carbonate. The aqueous layer is extracted with 1 ml of dichloromethane and the organic layer and extract combined and dried (Na$_2$SO$_4$). The solvent is removed and the residue chromatographed on two 20×20×20 0.2 cm thick layer silica gel plate with dichloromethane methanol conc. ammonium hydroxide (9:1.2:0.2) as solvent. The band containing product is separated, washed with methanol containing 5% ammonium hydroxide to give 0.084 g of solid.

REFERENCE EXAMPLE 53

2-[[2-Amino-3-(1H-imidazol-4-yl)-1-oxopropyl]-amino]-4,7-anhydro-1-cyclohexyl-1,2,5,6-L-arabino-Heptitol A solution of 2.51 g of $N^\alpha$, N(im)-dibenzyloxycarbonyl-L-histidine and 0.64 ml of N-methyl morpholine in 20 ml of ethyl acetate (under argon) is cooled to −23° C. To the solution is added 0.663 ml of isobutyl chloroformate and the mixture stirred for 30 minutes. To the solution is added 1.16 g of 2-amino-4,7-anhydro-1-cyclohexyl-1,2,5,6-tetra-deoxy-L-arabino-Heptitol and the mixture allowed to warm to 0° C. Additional 20 ml of ethyl acetate is added and the mixture stirred at room temperature for 1.5 hours. The mixture is diluted with 20 ml of ethyl acetate and washed with water, 2N-citric acid, 1M sodium bicarbonate and brine. The organic layer is dried ($Na_2SO_4$) and the solvent removed. The residue is crystallized from ethyl acetate-hexane to give 2.96 g of white crystals, mp. 125°–130° C.

As described for Reference Example 41, the preceding compound (2.5 g) and 3 g of ammonium formate in 60 ml of methanol under argon is treated with a suspension of 1.5 g of 10% palladium on carbon in 35 ml of water. The mixture is stirred (without cooling) for 1 hour and filtered through diatomaceous earth which is washed with methanol. The filtrate is concentrated and the aqueous residue made basic with concentrated ammonium hydroxide. Extraction with ethyl acetate and concentration of the extract gives the product as a solid; $[\alpha]_D^{26} -24 \pm 1(c, 1.003, CH_3OH)$

REFERENCE EXAMPLE 54

(S)-2-[(2-Amino-4-methyl-1-oxopentyl)amino]-1-cyclohexyl-1,2,4,5,6,7-hexadeoxy-4,7-epithio-L-arabino-heptitol To a solution of 0.997 g of tert-butyloxycarbonyl-L-leucine monohydrate and 444 1L of N-methylmorpholine in 10 ml of tetrahydrofuran chilled to 0° C. is added 516 1L of isobutyl chloroformate. After one minute, 1.09 g of 2-amino-1-cyclohexyl-1,2,4,5,6,7-hexadeoxy-4,7-epithio-L-arabino-Heptitol. The mixture is stirred at room temperature overnight and the solvent removed under vacuum. The residue in 25 ml of ethyl acetate is washed with 2N-citric acid (20 ml), 1M sodium bicarbonate (20 ml) and brine (20 ml). The organic layer is dried ($Na_2SO_4$) and the solvent removed to give 1.82 g of a white foam. A solution of preceding compound (1.66 g) in 20 ml of dichloromethane is chilled to 0° C. and 2.7 ml of trifluoroacetic acid added. The solution is stirred at 0° C. for 5 minutes and at room temperature for 2.5 hours. The solution is poured (with stirring) into cold 2N sodium hydroxide. The organic layer is separated and the aqueous layer extracted with dichloromethane (3×50 ml). The combined organic layer and extracts are dried ($Na_2SO_4$) and the solvent removed to give 1.3 g of a white foam.

REFERENCE EXAMPLE 55

(S)-4,7-anhydro-1-cyclohexyl-1,2,5,6-tetradeoxy-2-[[2-methylamino)3-[1-[(4-methylphenyl)sulfonyl]-1-H-imidazol-4-yl]-1-oxopropyl]amino]-L-arabino-Heptitol A mixture of 0.52 g of $N^\alpha$-(tert-butoxycarbonyl)-$N^{60}$-methyl-$N^{im}$-tosyl-L-histidine and 148 μL of N-methylmorpholine in 8 ml of tetrahydrofuran and 7 ml of ethylacetate is chilled to −23° C. and 153.65 μL of isobutyl chloroformate is added. After stirring at −23° C. for 0.5 hours, 0.269 g of 2-amino-4,7-anhydro-1-cyclohexyl-1,2,5,6-tetradeoxy-L-arabino-Heptitol is added. The mixture is stirred at −23° C. for one hour, at 0° C. for one hour and overnight at room temperature. The mixture is diluted with 25 ml of ethyl acetate and washed with water (10 ml), 2N citric acid (10 ml), 1M sodium bicarbonate (10 ml) and brine (10 ml). The organic layer is dried ($Na_2SO_4$) and the solvent removed to give a solid (0.65 g). Chromatography on silica gel thick layer plates (6) with 10% methanol in ethyl acetate gives 0.38 g of a solid. The solid is dissolved in dichloromethane-trifluoroacetic acid (1:1) and the solution stirred for 3 hours. The solvent is removed and to the residue in dichloromethane is added sodium bicarbonate solution. The organic layer is separated and the aqueous layer extracted with dichloromethane. The organic layer and extracts are combined, dried ($Na_2SO_4$) and the solvent removed to give the product as a solid.

REFERENCE EXAMPLE 56

2-[[2-Amino-3-[1-(2,4-dinitrophenyl)-1H-imidazol-4-yl]propyl]amino]-4,7-anhydro-1-cyclohexyl-1,2,5,6-tetradeoxy-L-arabino-Heptitol A solution of 2.554 g of $N^\alpha$-(tert-butoxycarbonyl)-$N^{im}$-(2,4-dinitrophenyl)-L-histidine and 0.64 ml of N-methylmorpholine in 20 ml of ethyl acetate is chilled to −23° C. and 0.663 ml of isobutyl chloroformate added. The mixture is stirred for 30 minutes at −23° C. and 1.16 g of 2-amino-4,7-anhydro-1-cyclohexyl-1,2,5,6-tetradeoxy-L-arabino-Heptitol added. The mixture is stirred at −23° for one hour, at 0° C. for one hour and 1.5 hours at room temperature. The mixture is diluted with 75 ml of ethyl acetate and washed with water (2×20 ml ), 1M sodium bicarbonate (20 ml), 2N citric acid (20 ml), brine (20 ml) and dried ($Na_2SO_4$). The solvent is removed to give 3.5 g of brown solid; $[\alpha]_D^{26} -14° \pm 1(c, 1.02, CH_3OH)$. To a 1.0 g sample of the preceding compound in 1.5 ml of dichlormethane, cooled to 0° C. is added 1.0 ml of trifluoroacetic acid. After two hours at room temperature, 0.5 ml of trifluoroacetic acid is added and the solution stirred for one hour. The solvent is removed under vacuum and water added to the residue. The mixture is made basic with ammonium hydroxide and extracted with ethyl acetate. The extract is dried ($Na_2SO_4$) and the solvent removed to give 0.8 g of a brown foam.

REFERENCE EXAMPLE 57

2-Bromoethyl 2-methylpropyl chlorophosphase

Prepared in a similar manner as Reference Example 46, from 2-methylpropanol, 2-bromoethanol, and phosphorus oxychloride.

REFERENCE EXAMPLE 58

[R (and S)]-N-[(2-Bromoethoxy)(2-methylpropoxy)phosphinyl]-L-phenylalanine

To a solution of L-phenylalanine methyl ester hydrochloride (1.09 g) and triethylamine (1.11 g) in dichloromethane (20 ml) is added 2.10 g of 2-bromoethyl 2-methylpropyl chlorophosphate. The mixture is stirred at room temperature for 4 hours. Saturated sodium bicarbonate (10 ml) is then added, and the dichloromethane is evaporated. The residue is diluted with water (10 ml), and extracted with 30 ml of ethyl acetate. The organic extract is washed with 10 ml portions of 1N hydrochloric acid, water, saturated sodium bicarbonate, and brine, dried over anhydrous sodium sulfate, filtered through hydrous magnesium silicate, and evaporated to give 2.23 g of a colorless gum, $[\alpha]_D^{26} +10° \pm 1$ g, 1.18, $CHCl_3$).

A solution of the above methyl ester (1.27 g) in methanol (18 ml) is treated with 6 ml of 1N sodium hydroxide at room temperature for one hour. The mixture is then diluted with water (6 ml) and the methanol is evaporated. The aqueous residue is washed with diethyl ether (10 ml) and then acidified to Ph 2 with 2N hydrochloric acid. The resulting mixture is extracted with 2×5 ml of ethyl acetate. The combined extracts are dried over anhydrous sodium sulfate, and evaporated to give 1.11 g of a colorless gum, $[\alpha\ _D^{26} +2° \pm 1$ g, 1.34, $CHCl_3$).

EXAMPLE 1

4,7-Anhydro-1-cyclohexyl-2-[[N-[3-cyclohexyl-N-(diethoryphosphinl-L-alanyl]-L-leucyl]amino]-1,2,5,6-tetradeoxy-L-arabino (and D-xylo)-Heptitol A 0.62 g sample of N-[N-diethoxyphosphinyl)-L-phenylalanyl-L-leuclyl]-(S)2-amino-3-cyclohexyl-(R)-1-(2-furanyl)propan-1-ol in 1 ml of methanol with 0.040 g of 5% rhodium on alumina is hydrogenated at 20 pounds per square inch in a Parr hydrogenator for 17 hours. The mixture is filtered through diatomaceous earth and the filter cake washed with methanol. The filtrate is concentrated to dryness to give 0.060 g of a white solid; $[\alpha]_D^{26} -45° \pm 2$ (c, 0.417, $CH_3OH$).

EXAMPLE 2

4,7-Anhydro-1,2,5,6-tetradeoxy-2-[N-(diethylphosphinyl)-L-phenylalanyl-L-leucylamino]-L-arabino-(and D-xylo)Heptitol A 0.060 g sample of Raney Nickel (50% in water) is washed with water until the pH of the wash is pH 8 and then the catalyst is washed with ethanol. To the catalyst is added 0.062 g of N-[N-diethoxyphosphinyl)-L-phenylalan-yl-L-leucyl]-(S)-2-amino-3-cyclohexyl-(R)-1-(2-furanyl)pro-pan-1-ol and 4 ml of ethanol. The mixture is hydrogenated at 50-55 pounds per square inch in a Parr hydrogenator for 20 hours. The mixture is filtered through diatomaceous earth, the filter cake washed with ethanol and the filtrate concentrated to dryness. The residue is dissolved in ethyl acetate and the solution washed with brine, dried ($Na_2SO_4$) and the solvent removed to give 0.062 g of white solid $[\alpha]_D^{26} -37° \pm 2$ (c, 0.644 g $CH_3OH$).

EXAMPLE 3

[S-(Re,R*)]=4,7-Anhydro-1-cyclohexyl-1,2,5,6-tetradeoxy-2-[[2-[[2-[(diethoxyphosphinyl)-oxy)1-1-oxo-3-phenylpropyl]amino]-4-methyl-1-oxopentyl]amino]-L-arabino(and D-xylo)Heptitol A 0.50 g sample of Raney Nickel (50% in water) is washed with water until the pH of the wash is pH 8 and then the catalyst is washed with ethanol. To this Raney Nickel is added 0.31 g of diethyl [1S-[1R*,2-[1R-*(1R*,2S*)]]]-2-[[1-[[[1-(cyclohexylmethyl)-2-(2-furanyl)-2-hydroxyethyl]amino]carbonyl]-3-methylbutyl]amino]-2-oxo-1-(phenylmethyl)ethyl phosphate, 10 ml of ethanol and the mixture hydrogenated at 50 pounds per square inch in a Parr hydrogenator for 2 days. The mixture is filtered through diatomaceous earth and the filter cake washed with ethanol. The filtrate is evaporated and the residue chromatographed on silica gel with ethyl acetate-hexane (2:1) to give 0.30 g of white solid; $[\alpha]_D^{26} -58° \pm 1$ (c, 0.988, $CHCl_3$).

EXAMPLE 4

Diethyl [1S-[1R*,2[1R*,2S*)]]]-2-[[1-[[[1-(Cyclohexylmethyl)-2-(2-furanyl)-2-hydroxyethyl]amino]carbonyl]-3-methylbutyl]amino]-2-oxo-1-(phenylmethyl)ethyl phosphate A mixture of 0.078 g of phenyl dichlorophosphate and 0.12 g of imidazole in 1 ml of dichloromethane is stirred at room temperature for 0.5 hour. To the mixture, chilled to −15° C., is added 0.15 g of (S)-N-[2-[(diethoxyphosphinyl)oxy]-1-oxo-3-phenylpropyl]-L-leucine in 0.5 ml of dichloromethane. The mixture is stirred (−15° C.) for 1 hour and 0.067 g of (S)-2-amino-3-cyclohexyl-(R)-1-(2-furanyl)propan-1-ol in 0.5 ml of dichloromethane added. The mixture is stirred at −15° C. for 26 hours and the solvent removed. The residue is dissolved in 2 ml of ethanol, 1 ml of 1N sodium hydroxide added and the mixture stirred for 0.5 hour. Water (4 ml) is added and the mixture concentrated under vacuum. The aqueous phase is decanted and the solid residue washed with water. The solid is dissolved in 15 ml of ethyl acetate and the solution washed with 5 ml each of 1N hydrochloric acid, saturate d sodium bicarbonate, brine and dried ($Na_2SO_4$). The solvent is removed and the residue (0.18 g) chromatographed on silica gel with ethyl acetate-hexane (1:1) to give 0.15 g of white foamy solid:$[\alpha]_D^{26} -60° \pm 1$ (c, 0.662,$CHCl_3$).

EXAMPLE 5

[S-(R*,R*)]-4,7-Anhydro-1-cyclohexyl-1,2,5,6-tetradeoxy-2-[[2-[(2-hydroxy-1-oxo-3-phenylpropyl)amino-4-methyl-1-oxopentyl]amino-L-arabino-Heptitol A solution 0.10 g of L-3-(phenyl)lactic acid in 0.5 ml of tetrahydrofuran is added to a solution of 0.058 g of bis(trichloromethyl)carbonate (triphosgene) in 1 ml of tetrahydrofuran under argon. After 5 minutes at room temperature, 0.27 g of 1,8-bis(dimethylamino)naphthalene in 0.5 ml of tetrahydrofuran is added and the mixture stirred in the dark for 4 hours. To the mixture is added 0.13 g of (S)-2-[(2-amino-4-methyl-1-oxopentyl)amino] 4,7-anhydro-1-cyclohexyl-1,2,5,6-tetradeoxy-L-arabino-Heptitol. The mixture is stirred at room temperature for 18 hours. To the mixture is added another portion of L-3-(phenyl)lactic acid, bis(trichloromethyl)- carbonate and 1,8-bis(dimethylamino)naphthalene in tetrahydrofuran prepared as previously described. After stirring for 3 hours, the mixture is filtered and diluted with 15 ml of ethyl acetate. The organic solution is washed twice with 5 ml of 1N hydrochloric acid and once with 5 ml portions of water, sodium bicarbonate, brine and dried (Na$_2$SO$_4$). The solution is filtered through a thin pad of hydrous magnesium silicate, the pad washed with ethyl acetate and the filtrate evaporated. The residue is washed with ether-hexane to give 0.16 g of white solid; 8 $\alpha]_D^{26} - 88° \pm 1$ (c, 0.737, CHCl$_3$).

EXAMPLE 6

[S-(R*,R*)]-4,7-Anhydro-1-cyclohexyl-2[[2-[[3-cyclohexyl-2-[(diethoxyphosphinyl)oxy]-1-oxopropyl]amino]-4-methyl-1-oxopentyl]amino]-1,2,5,6-tetradeoxy-L-arabino-(and D-xylo)-Heptitol A mixture of 0.19 g of diethyl [1S-[1R*,2-[1R*-(1R*,2S*)]]]-2-[[1-[[[1-(cyclohexylmethyl)-2-(2-furanyl)-2-hydroxyethyl]amino]cabonyl]-3-methylbutyl]amino]-2-oxo-1-(phenylmethyl)ethyl phosphate, 0.120 g of 5% rhodium on alumina in 3 ml of dry methanol is hydrogenated in a Parr hdyrogenator at 20 pounds per square inch for 40 hours at room temperature. The mixture is filtered through diatomaceous earth, the filter pad washed with methanol and the filtrate evaporated. The residue (0.22 g) is chromatographed on silica gel with ethyl acetate-hexane (1:1) and then ethyl acetate-hexane (2:1) as eluent to give 0.16 g of white glass; $[\alpha]_D^{26} - 64° \pm 2$ (c, 0.569, CHCl$_3$).

EXAMPLE 7

Diethyl [1S-[1R*,2[1R*(1R*,2S*)]]]-2-[[1-[[[1-(cyclohexylmethyl)-2-hydroxy-2-(2-thienyl)ethyl]amino]carbonyl]-3-methylbutyl]amino-2-oxo-1-(phenylmethyl)ethyl phosphate A mixture of 0.17 g of phenyl dichlorophosphate and 0.27 g of imidazole in 2 ml of dichloromethane is stirred at room temperature for 0.5 hour. To the mixture chilled to $-15°$ C. is added 0.33 g of (S)-N-[2-[(diethoxy-phosphinyl)oxo]-1-oxo-3-phenylpropyl]-L-leucine in 2 ml of dichloromethane. The mixture is stirred at $-15°$ C. for 1 hour and 0.12 g of (S)-2is amino-3-cyclohexyl-(R)-1-(2-thienyl)propan-1-ol in 1 ml of dichloromethane. The mixture is stirred overnight at $-15°$ C. The solvent is removed and 20 ml of ethyl acetate and 10 ml of water added. The organic layer is separated and washed with 1N hydrochloric acid, water and saturated sodium bicarbonate and brine. The organic layer is dried (Na$_2$SO$_4$) and the solvent removed. The residue is chromatographed on silica gel with ethyl acetate-hexane (1:1) as eluent to give 0.090 g of a gum; $[\alpha]_D^{26} - 57° \pm 1$ (c, 0.842, CHCl$_3$).

EXAMPLE 8

4,7-Anhydro-1-cyclohexyl-1,2,5,6-tetradeoxy-2-[N-(diethoxyphosphinyl-L-phenylalanyl-L-leucylamino]-L-arabino-Heptitol As described for Example 4, 0.17 g of N-[N-(diethoxylphosphinyl)-L-phenylalanyl]-L-leucine is coupled with 0.045 g of 2-amino-4,7-anhydro-1-cyclo-hexyl-1,2,5,6-tetradeoxy-L-arabino-Heptitol in 2 ml of dichloromethane to give 0.11 g of a white solid; $[\alpha]_D^{26} - 36° \pm 1$ (g, 0.819, CH$_3$OH).

EXAMPLE 9

[S-(R*,R*)]-4,7-Anhydro-1-cyclohexyl-1,2,5,6-tetradeoxy-2-[[2-[[2-[(diethoxyohosphinyl)oxy)1-1-oxo-3-phenylpropyl]amino]-4-methyl-1-oxopentyl]amino-L-arabino-Heptitol As described for Example 4, 0.15 g of (S)-N-[2-[(diethoxyphosphinyl)oxy]-1-oxo-3-phenylpropyl]-L-leucine is coupled with 2-amino-4,7-anhydro-1-cyclohexyl-1,2,5,6-tetradeoxy-L-arabino-Heptitol in 2 ml of dichloromethane to give 0.50 g of white solid; $[\alpha]_D^{26} - 52° \pm 4$ (c, 0.244, CHCl$_3$).

EXAMPLE 10

N(1S)-[N[1R ,1(1R*,2S*)], alpha R*]]-N-[1-[[[1-Cyclohexylmethyl)-2-(2-furanyl)-2-hydroxyethyl]amino]carbonyl]-3-methylbutyl]-aloha-hydroxybenzenepropanamide A 0.076 g sample of L-3-(phenyl)lactic acid in 1-ml of tetrahydrofuran is added to 0.045 g of bis(trichloromethyl)carbonate (triphosgene) in 4-ml of tetrahydrofuran. After 5 minutes 0.25 g of 1,8-bis(dimethylamino)naphthalene in 1 ml of tetrahydrofuran is added. After 30 minutes in the dark, 0.10 g of N-(L-leucyl)-(S)-2-amino-3-cyclohexyl-(R)-1-(2-furanyl)propan-1-ol is added and the mixture stirred 23 hours. A second portion of 0.076 g of L-3-(phenyl)lactic acid, 0.045 g of bis (trichloromethyl)-carbonate, 0.25 g of 1,8-bis(dimethylamino)naphthalene in 5 ml of tetrahydrofuran (prepared as previously described) is added. The mixture is stirred for 3 hours, filtered and the filtrate evaporated. The residue is dissolved in 2 ml of methanol and 1.0 ml of 1N sodium hydroxide added. The mixture is stirred 0.5 hour, diluted with water, concentrated and extracted with ethyl acetate (10 ml). The extract is washed with 1N hydrochloric acid, sodium bicarbonate, brine and dried (Na$_2$SO$_4$). The solvent is removed to give 0.13 g of solid which is washed with a small amount of isooctane to give 0.12 g of white solid; $[\alpha]_D^{26} - 92° \pm 1$ (c, 0.760, CHCl$_3$).

EXAMPLE 11

[S-(R*,R*)]-4,7-Anhydro-1-cyclohexyl-2-[[2-[(3-cyclohexyl-2-hydroxy-1-oxopropyl)amino[-4-methyl-1-oxopentyl]amino]-1,2,5,6-tetradeoxy-L-arabino-Heptitol As described for Example 1, 0.073 g of Example 10 in 3-ml of methanol is hydrogenated in a Parr hydrogenator with 0.060 g of rhodium on alumina at 20 pounds per square inch of hydrogen for 4 hours to give 0.072 g of a white solid; $[\alpha]_D^{26} - 63° \pm 1$ (C, 0.686, CH$_3$OH).

EXAMPLE 12

(S)-4,7-Anhydro-2-[[2-[[bis(phenylmethoxy)phosphinyl]amino]-4-methyl-1-oxopentyl]amino]-1-cyclohexyl-1,2,5,6-tetradeoxy-L-arabino-Heptitol To a solution of 0.20g (0.75 mmol) of dibenzylphosphite in carbon tetrachloride (1.5 ml) is added 1.5 ml of triethylamine. The mixture is stirred for 15 minutes at room temperature. A solution of 0.17 g (0.5 g mmol) of the L-arabino-Heptitol from Reference Example 19 in tetrahydrofuran (2 ml) is then added, and the mixture is stirred for 24 hours. The solvents are evaporated under reduced pressure, and residue is dissolved in ethyl acetate (30 ml). The solution is then washed with 1N hydrochloric acid (10 ml), 1N sodium hydroxide (2×10 ml), and brine (10 ml) dried over anhydrous sodium sulfate, filtered through Magnesol (hydrous magnesium silicate), and evaporated under reduced pressure. The residue is triturated with hexanes to give 0.26 g of a white solid, $[\alpha]_D^{26} -34°\pm 2$ (C,0.569, CHCl$_3$).

EXAMPLE 13

[R-(R*,Se) and S-(R*,R*)]-2-[[2-[[[2-(acetylamino)ethoxy](3-phenylpropyl)phosphinyl]amino]-4-methyl-1-oxopentyl]amino]-4,7-anhydro-1-cyclohexyl-1,2,5,6-tetradeoxy-L-arabino-Heptitol Prepared in a similar manner as Example 12 from the L-arabino-Heptitol of Reference Example 19 and 2-(acetylamino)ethyl 3-phenylpropylphosphinate $[\alpha]_D^{26} -21°\pm 1$ (C, 0.802, CHCl$_3$).

EXAMPLE 14

[R-(R*,S*) and S-(R*,R*)1-4,7-anhydro-1-cyclohexyl-1,2,5,6-tetradeoxy-2-[[3-[[methoxy(3-phenylpropyl)phosphinyl]amino]-4-methyl-1-oxopentyl]amino]-L-arabino-Heptitol Prepared in a similar manner as Example 12 from the L-arabino-Heptitol of Reference Example 19 and methyl 3-phenylpropylphosphinate $[\alpha]_D^{26} -30°\pm 2$ (C, 0.425, CHCl$_3$).

EXAMPLE 15

[R=(R*,S*) and S-(R*,R*)]-4,7-Anhydro-1-cyclohexyl-1,2,5,6-tetradeoxy-2-[[4-methyl-1-oxo-2-[(phenoxy[[[phenylmethoxy)carbonyl]amino]oxy]phosphiny]amino]pentyl]amino]-L-arabino-Heptitol A solution of 68 mg (0.2 mmol) of the L-arabino-heptitol from Reference Example 19 in dichloromethane (2 ml) is treated with 40 mg (0.4 mmol) of triethylamine, and 1 ml of a 0.4M solution of phenyl phenylmethoxycarbonylamino chlorophosphate in diethyl ether. The mixture is stirred for 18 hours at room temperature. The resulting suspension is diluted with ethyl acetate (15 ml), and washed with 1N hydrochloric acid (5 ml) 1N sodium hydroxide (3×5 ml) and brine (5 ml). The organic solution is dried over anhydrous sodium sulfate, filtered through Magnesol, and evaporated under reduced pressure to give 70 mg of a white solid.

EXAMPLE 16

(S)=4,7-Anhydro-2-[[2-[[bis(phenoxy)phosphinyl]amino]-4-methyl-1-oxopentyl]amino]-1-cyclohexyl-1,2,5,6-tetradeoxy-L-arabino-Heptitol Prepared in a similar manner as Example 15 from the L-arabino-Heptitol of Reference Example 19 and diphenyl chlorophosphate $[\alpha]_D^{26} -34°\pm 1$ (C, 1.000, CHCl$_3$).

EXAMPLE 17

4,7,-Anhydro-1-cyclohexyl-1,2,5,6-tetradeoxy-2-[N-(diethoxyphosphinyl)-L-phenylalanyl-L-leucylamino-]-D-xylo-Heptitol As described for Example 4, 0.25 g of N-[N-(diethoxyphosphinyl)-L-phenylalanyl]-L-leucine is coupled with 0.068 g of 2-amino-4,7-anhydro-1-cyclohex-yl-1,2,5,6-tetradeoxy-D-xylo-Heptitol in 3 ml of dichloromethane to give 0.15 g of a white solid $[\alpha]_D^{26} -42°\pm 1$ (C, 0.796, CHCl$_3$).

EXAMPLE 16

(S)-4,7-Anhydro-2-[[2-[[bis(phenoxy)phosphinyl]amino]-4-methyl-1-oxopentyl]amino]-1-cyclohexyl-1,2,5,6-tetradeoxy-L-arabino-Heptitol Prepared in a similar manner as Example 15 from the L-arabino-Heptitol of Reference Example 19 and diphenyl chlorophosphate $[\alpha]_D^{26} -\pm 1$ (C, 1.000, CHCl$_3$).

EXAMPLE 17

4,7,-Anhydro-1-cyclohexyl-1,2,5,6-tetradeoxy-2-[N-(diethoxyphosphinyl)-L-phenylalanyl-L-leucylamino-]-D-xylo-Heptitol As described for Example 4, 0.25 g of N-[N-(diethoxyphosphinyl)-L-phenylalanyl]-L-leucine is coupled with 0.068 g of 2-amino-4,7-anhydro-1-cyclohex-yl-1,2,5,6-tetradeoxy-D-xylo-Heptitol in 3 ml of dichloromethane to give 0.15 g of a white solid $[\alpha]_D^{26} -42°\pm 1$ (C, 0.796, CHCl$_3$).

EXAMPLE 18

R-(R*,S*)and S-(R*,R*)]-4,7-Anhydro-1-cyclohexyl-1,2,5,6-tetradeoxy-2-[[2-[hydroxy(3-phenylpropyl)phosphinyl]amino]-4-methyl-1-oxopentyl]amino]-L-arabino-Heptitol,p-ester with 1,2:3,4-bis-O-(1-methylethylidene)-alpha-D-galactopyranose Prepared in a similar manner as Example 12 from Reference Examples 19 and 43, $[\alpha]_D^{26} -47°\pm 1$ (c, 0.700, CHCl$_3$).

EXAMPLE 19

[R-(R*,S*) and S-(R*,R*)1-4,7-Anhydro-1-cyclohexyl-1,2,5,6-tetradeoxy-2-[[2-[[(2-phenylethoxy)(3-phenylpropyl)phosphinyl]amino]-4-methyl-1oxopentyl]amino]-L-arabino-Heptitol Prepared in a similar manner as Example 12 from Reference Examples 19 and 44, $[\alpha]_D^{26} -29°\pm 1$ (c, 76, CHCl$_3$).

EXAMPLE 20

4,7-Anhydro-2-[]2-[[bis(2-phenylethoxy)phosphinyl]amino]-4-methyl-1-oxopentyl amino]-1-cyclohexyl-1,2,5,6-tetradeoxy-L-arabino-Heptitol Prepared in a similar manner as Example 21, using bis(2-phenylethyl)chlorophosphate (Reference Example 45) as the reagent, $[\alpha]_D^{26} -30°\pm 1$ (c, 0.62, CHCl$_3$).

EXAMPLE 21

[R-(R*,S*) and S-(R*,R*)]-4,7-Anhydro-2-[[2-[[(2bromoethoxy)(2-phenylethoxy)phosphinyl]amino]-4-methyl-1-oxopentyl]amino]-1-cyclohexyl-1,2,5,6-tetradeoxy-L-arabino-Heptitol To a solution of 0.34 g (1 mmol) of Reference Example 19 in dichloromethane (4 ml) is added 0.20 g (2 mmol) of triethylamine, followed by the addition of 0.49 g (1.5 mmol) of Reference Example 46. The mixture is stirred at room temperature for two hours. A solution of saturated sodium bicarbonate (4 11) is then added, and the dichloromethane is evaporated. The residue is extracted with 30 ml of ethyl acetate, and the organic solution is washed with 10 ml portion of 1 N hydrochloric acid, water, saturated sodium bicarbonate solution, and brine. Drying over anhydrous sodium sulfate and evaporation of solvents gives 0.64 g of crude material which is chromatographed with a silica gel column to yield 0.57 g of a colorless gum, $[\alpha]_D^{26} -32°\pm2$ (c,0.56, CHCl$_3$).

EXAMPLE 22

R-(R*,S*)and S-(R*,R*)]-4,7-Anhydro-1-cyclohexyl-1,2,5,6-tetradeoxy-2-[[2-[[[2-(dimethylamino) ethoxy](2-phenylethoxy)phosphinyl]amino]-4-methyl-1-oxopentyl]amino]L-arabino-Heptitol, hydrochloride A solution of 0.12 g (0.19 mmol) of Example 21 and 0.5 ml of dimethylamine in chloroform (1 ml) is heated at 60° C. in a pressure bottle for 2 hours. The volatiles are then evaporated, and the residue is partitioned between 5 ml of saturated sodium bicarbonate solution and 15 ml of diethyl ether. The organic solution is washed with 5 ml of brine, dried over anhydrous sodium sulfate, and then located with 2 ml of 1N HCl in diethyl ether, and dried in vacuo to give 0.13 g of a white foamy glass, $[\alpha]_D^{26} -27°\pm2$ (c, 0.806, CHCl$_3$).

EXAMPLE 23

4,7-Anhydro-1-cyclohexyl-1,2,5,6-tetradeoxy-2-[[4-methyl-1-oxo-2- [[2-phenylethoxy) [2-[(2-pyridinylmethyl)amino[ethoxy]phosphinyl]amino]pentyl]amino]-L-arabino-Heptitol,dihydrochloride Prepared in a similar manner as Example 24, using 2-aminomethylpyridine as the reagent, $[\alpha]_D^{26} -26°\pm1$ (c, 0.84, CHCl$_3$).

EXAMPLE 24

[R-(R*,S*) and S-(R*,R*)]-4,7-Anhydro-1-cyclohexyl-1,2,5,6-tetradeoxy -2-[[4-methyl-1-oxo-2-[[(2-phenylethoxy)[2-[(3-pyridinylmethyl)amino]ethoxy]phosphinyl]amino]pentyl]amino]-L-arabino-Heptitol,dihydrochloride To a solution of 63 mg (0.1 mmol) of Example 21 and 0.32 g (3.0 m mmol) of 3-aminomethylpyridine in chloroform (1 ml) is heated with stirring at 65° C. for 3 hours. The mixture is diluted with 10 ml of water and 2 ml of saturated bicarbonate solution, and the chloroform is evaporated. The residue is extracted with diethyl ether (15 ml). The extract is washed with 3×10 ml of water and 5 ml of brine, and dried over anhydrous sodium sulfate. It is then treated with 0.5 ml of 1N HCl in diethyl ether. The suspension is filtered, the precipitate is dried in vacuo to give 70 mg of a white solid, $[\alpha]_D^{26} -24°\pm1$ (c,0.75, CHCl$_3$).

EXAMPLE 25

[R-(R*,S*) and S-(R*,R*)]-4,7-Anhydro-1-cyclohexyl-1,2,5,6-tetradeoxy -2-[[4-methyl-1-oxo-2-[[[2(3-oxo-1-piperazinyl) ethoxy](2-phenylethoxy)phosphinyl]amino]pentyl]amino]-L-arabino-Heptitol,dihydrochloride Prepared in a similar manner as Example 24, using 2-ketopiperazine as the reagent, $[\alpha]_D^{26} -27°\pm2$ (c, 0.728, CHCl$_3$).

EXAMPLE 26

[R-(R*,S*) and S-(R*,R*)]-4,7-Anhydro-1-cyclohexyl-1,2,5,6-tetradeoxy -2-[[4-methyl-1-oxo-2-[[(phenylethoxy)[[(phenylmethyl)amino]ethoxy]phosphinyl]amino]pentyl]amino]-L-arabino-Heptitol,dihydrochloride Prepared in a similar manner as Example 24, using benzylamine as the reagent, $[\alpha]_D^{26} -23°\pm1$ (c, 0.982, CHCl$_3$).

EXAMPLE 27

[R-(R*,S*) and S-(R*,R*)]-4,7-Anhydro-1-cyclohexyl-1,2,5,6-tetradeoxy -2-[[2-[[[2-[[(1-hydroxycyclohexyl) methyl]amino]ethoxy](2-phenylethoxy) phosphinyl]amino]-4-methyl-1-oxopentyl]amino]-L-arabino-Heptitol,dihydrochloride Prepared in a similar manner as Example 24, using 1-aminomethyl-1-cyclohexnol as the reagent, $[\alpha]_D^{26} -21°\pm1$ (c, 0.88, CHCl$_3$).

EXAMPLE 28

[R-(R*,S*) and S-(R*,R*)]-4,7-Anhydro-2-[[2-[[(3-bromopropoxy)(2-phenylethoxy)phosphinyl]amino 4-methyl-1-oxopentyl]amino]-1-cyclohexyl-1,2,5,6-tetradeoxy-L-arabino-Heptitol,dihydrochloride Prepared in a similar manner as Example 21, using the chlorophosphate from reference Example 47 as the reagent, $[\alpha]_D^{26} -30°\pm1$ (c, 0.85, CHCl$_3$).

EXAMPLE 29

[R-(R*,S*) and S-(R*,R*)]-4,7-Anhydro-1-cyclohexyl-1,2,5,6-tetradeoxy -2-[[4-methyl-1-oxo-2-[[(2-phenylethoxy) [2-[(4-pyridinylmethyl)amino]ethoxyphosphinyl]amino]-pentyl]amino]-L-arabino-Heptitol,dihydrochloride Prepared in a similar manner as Example 24, using 4-aminomethylpyridine as the reagent, $[\alpha]_D^{26} -32°\pm2$ (c, 0.725, CHCl$_3$).

EXAMPLE 30

4,7-Anhydro-1-cyclohexyl-1,2,5,6-tetradeoxy-2-[N-(diisobutoxyphosphinyl-L-phenylalanyl-L-leucylamino]-L-arabino-Heptitol As described for Example 4, 0.71 g of N-[N-(diisobutoxyphosphinyl)-L-phenylalanyl]-L-leucine (Reference Example 49) is coupled with 0.11 g of 2-amino-4,7-anhydro-1-cyclohexyl-1,2,5,6-tetradeoxy-L-arabino-Heptitol (Reference Example 31) to give 0.32 g of a white solid; $[\alpha]_D^{26} -41°\pm1$ (c, 0.885, CHCl$_3$).

EXAMPLE 31

(S,S,S,R,S)-4,7-Anhydro-1-cyclohexyl-1,2,5,6-tetradeoxy-2-[[N-[N-(diethoxyphosphinyl-3-cl-naphthalonyl)-L-alanyl]-L-leucyl]amino]-L-arabino-Heptitol As described for Reference Example 15, 0.25 g of N-(diethoxyphosphinyl)-L-3-(1'-naphthyl)alanine is coupled with 0.15 g of (s)-2-[(2-amino-4-methyl-1-oxopentyl)amino]4,7-anhydro-1-cyclohexyl-1,2,5,6-tetradeoxy-L-arabino-Heptitol to give 0.28 g of a white solid; $[\alpha]_D^{26} -70° \pm 1$ (c, 0.877, CHCl$_3$).

EXAMPLE 32

1-Cyclohexyl-1,2,4,5,6,7-hexadeoxy-2-[[N-[N-(diethoxyphosphinyl)
-L-phenylalanyl]-4-leucyl]amino]4,7-epithio-L-arabino-Heptitol As described for Example 4, 0.75 g of N-[N-(diethoxyphosphinyl)-L-phenylalanyl]-L-leucine is coupled with 0.15 g of 2-amino-1-cyclohexyl-1,2,4,5,6,7-heaxdeoxy-4,7-epithio-L-arabino-Heptitol to give 0.38 g of a white solid; $[\alpha]_D^{26} -28° \pm 1$ (c, 1.075, CHCl$_3$).

EXAMPLE 33

[R-(R*,S*) and S-(R*,R*)]-4,7-Anhydro-1-cyclohexyl-1,2,5,6-tetradeoxy -2-[[2-[[(2-phenylethoxy) (3-phenylpropyl)phosphinyl]amino]-4-methyl-1-oxopentyl]amino]-L-arabino-Heptitol To a solution of 1.21 g of N,N,carbonyldiimidazole in 10 ml of tetrahydrofuran under argon is added a solution of 3.12 g of Reference Example 50 in 5 ml of tetrahydrofuran. The mixture is stirred for one hour at room temperature and a solution of 2-amino-4,7-anhydro-1-cyclohexyl-1,2,5,6-tetradeoxy-L-arabino-Heptitol in 5 ml of tetrahydrofuran is added. The solution is stirred at room temperature overnight and then diluted with 15 ml of water and 15 ml of saturated sodium bicarbonate. The mixture is concentrated under vacuum and a gum separated. The water is decanted from the gum and the gum washed with water (2×15 ml). The gum is dissolved in 50 ml of dichloromethane and the solution washed with 1N HCl (25 ml), saturated NaHCO$_3$ (25 ml) and brine (25 ml). The organic layer is dried (Na$_2$SO$_4$) and the solvent removed to give 3 g of a gun. Flash chromatography on silica gel with ethyl acetate as eluent gives 1.4 g of a white solid, mp 104°–110° C.

EXAMPLE 34

[R-(R*,S*) and S-(R*,R*)]-4,7-Anhydro-1-cyclohexyl-1,2,5,6-tetradeoxy -2-[[2-[[hydroxy(3-phenylpropyl) phosphinyl]amino]-4-methyl-1-oxopentyl]amino]-L-arabino-Heptitol, (p-6)ester with α-D-galactopyranose A 0.100 g sample of Example 1 in a mixture of 2 ml of acetic, and 3 ml of CH$_3$OH and 0.5 ml of water is stirred for 5 hours, diluted with water 5 ml and extracted with ethyl acetate. The extract is washed with water, dried and the solvent removed to give the product as a glass.

EXAMPLE 35

4,7-Anhydro-1-cyclohexyl-1,2,5,6-tetradeoxy-2-[[N-[N-(diethoxyphosphinyl)-L-phenylalanyl]-N-methylhistidyl]amino]-L-arabino-Heptitol To a solution of 0.301 g of N(diethoxyphosphinyl)-L-phenylaline and 0.11 g of triethylamine in 15 ml of dichloromethane is added 0.442 g of benzotriazol-1-yloxytris(dimethylamino)phosphonium hexafluorophosphate (BOP). After stirring one minute, 1 mmol of (S)-4,7-anhydro-1-cyclohexyl-1,2,5,6-tetradeoxy-2-[[ 2-(methylamino)-3-[1-[1-[(4-methylphenyl)sulfonyl]-1H-imidiazol-4-yl]-1-oxopropyl]amino]L-arabino-Heptitol is added. The mixture is stirred at room temperature overnight and the solvent removed. To the residue in 15 ml of methanol is added 1-hydroxybenzotriazole (0.153 g) and the mixture stirred for 12 hours. The solvent is removed and the residue i ethyl acetate is washed with sodium carbonate, 1N citric acid and with brine. The solvent is removed and the residue chromatographed on silica gel with dichloromethane-methanol-triethylamine as solvent to give the product as a solid.

EXAMPLE 36

4,7-Anhydro-1-cyclohexyl-1,2,5,6-tetradeoxy-2-[[N-[N-(diethoxyphosphinyl)O-methyl-L-tryosyl]-L-histidyl]amino]-L-arabino-Heptitol To a solution of 0.160 g of N-(diethoxyphosphinyl)-L-(4-methoxyphenyl)alanine in 6 ml of dichloromethane is added 0.53 ml of triethylamine and 0.221 g of benzotriazol-1-yloxytrix(dimethylamino)phosphonium hexafluorophosphate (BOP). After stirring for 1 minute, 0.114 g of 2-[[2-amino-3-(1H-imidazol-4-yl)-1-oxopropyl]amino]-4,7-anhydro-1-cyclohexyl-1,2,5,6-tetradeoxy-L-arabino-Heptitol. The mixture is stirred overnight and the solvent removed. The residue is dissolved in ethyl acetate and washed with water, 2N sodium carbonate and dried (Na$_2$SO$_4$). The solvent is removed and the residue purified by chromatography on silica gel with dichloromethane-methane-triethylamine as solvent to give the product as a solid.

EXAMPLE 37

1-Cyclohexyl-1,2,4,5,6,7-hexadeoxy-2-[[N-[N-(diethoxyphosphinyl)
-L-phenylalanyl]-4-leucyl]amino]4,7-epithio-L-arabino-Heptitol,S-dioxide A solution of 0.064 g of Example 32 in dichloromethane is treated with 0.14 g of 3-chloroperoxybenzoic acid (50-60%), and the mixture is stirred at room temperature for 20 hours. It is then quenched with 2 ml of saturated sodium bicarbonate solution and 2 ml of saturated sodium sulfite solution. The mixture is extracted with 10 ml of ethyl acetate.

The organic extract is washed with brine (5 ml), dried over anhydrous sodium sulfate, and evaporated to give 0.070 g of a white solid; $[\alpha]_D^{26} -61° \pm 2$ (c, 0.787, CHCl$_3$).

EXAMPLE 38

[R(and S)]-2-[N-[N-[(2-bromoethoxy)(2-methylpropoxy) phosphinyl]L-phenylalanyl]L-leucyl]amino]1-cyclohexyl-1,2,4,5,6,7-hexadeoxy--4,7-epithio-L-arabino-Heptitol As described for Reference Example 15, 1.02 g of [R(and S)]-N-[2-bromoethoxy)(2-methylpropoxy)-phosphinyl]L-phenylalanine is coupled with 0.43 g of (S)-2-[(2-amino-4-methyl-1-oxopentyl)amino]1-cyclohexyl-1,2,4,5,6,7-hexadeoxy-4,7-epithio-L-arabino-Heptitol to give 0.70 g of a white solid; $[\alpha]_D^{26} -26° \pm 1$ (c, 1.072, CHCl$_3$).

EXAMPLE 39

[R(and S)]-1-Cyclohexyl-1,2,4,5,6,7-hexadeoxy--4,7-epithio-2-[[N-[N-[(2-methylpropoxy)[2-(4-morpholinyl)ethoxy]phosphinyl]L-phenylalanyl]-L-leucyl]amino]-L-arabino-Heptitol,monohydrochloride A mixture of Example 38 (0.15 g) and morpholine (0.35 g) in chloroform (1 ml) is heated at 55° for two hours. It is then treated with 2 ml of water and 1 ml of saturated sodium bicarbonate solution, and the chloroform is evaporated. The aqueous phase is decanted, and the residue is washed with water. The residue is then dissolved in ethyl acetate (15 ml), washed with water (5 ml) and brine (5 ml), dried over anhydrous sodium sulfate, and evaporated to about 5 ml in volume. The solution is treated with 1N HCl in diethyl ether until no further precipitation occurs. The precipitate is dried in vacuo to give 0.12 g of a white solid; $[\alpha]_D^{26} -30° \pm 2$ (c, 0.621, CHCl$_3$).

EXAMPLE 40

4,7-Anhydro-1-cyclohexyl-1,2,5,6-tetradeoxy-2-[[N-[N-(diethoxyphosphinyl-L-3-(1'-naphthyl)alanyl]-L-histidyl]amino]-L-arabino-Heptitol As described for Reference Example 15, 0.30 g of N-(diethoxyphosphinyl)-L-3-(1'-naphthyl)alanine is coupled with 0.32 g of (S)-2-[[2-amino-3-[1-(2,4-dinitrophenyl)-1H-imidazol-4-yl]-1-oxopropyl]-amino]4,7-anhydro-1-cyclohexyl-1,2,5,6-tetradeoxy-L-arabino-heptitol and the resulting product is treated with 1N sodium hydroxide (2 ml) in methanol (4 ml) to give 0.38 g of an off-white solid; $[\alpha]_D^{26} -47° \pm 4$ (c, 0.257, 1N HCl—MeOH).

We claim:

1. A compound of the formula I:

$$R_1\left(W-\overset{R_2}{\underset{*}{CH}}-\overset{O}{\overset{\|}{C}}\right)_q\overset{R_4}{\underset{R_3}{C}}-\overset{*}{CH}-\overset{O}{\overset{\|}{C}}-N-\overset{R_6}{\underset{R_5}{CH}}-\overset{OH}{\underset{*}{CH}}-A$$

wherein
R is

[structures shown: cyclic phosphate structures with B, (CH$_2$)$_m$, (CH$_2$)$_p$ groups; phenylmethyl-O and alkyl(C$_1$–C$_6$)—O variants with B substituent and N—O—R$_{10}$]

[alkyl(C$_1$–C$_6$)O] [phenylmethyl-O]—P(=O)—,

[alkyl(C$_1$–C$_6$)O]$_2$P(=O)—, (phenyl-O)$_2$P(=O)—,

[alkyl(C$_1$–C$_6$)] [alkyl-(C$_1$–C$_6$)O]P(=O)—, (phenylmethyl-O)$_2$P(=O)—, [alkyl(C$_1$–C$_6$)O] [phenyl-O]P(=O)—,

[phenyl(CH$_2$)$_n$O]$_2$—P(=O)—, [phenyl(CH$_2$)$_n$] [phenyl(CH$_2$)$_n$O]—P(=O)—,

[phenyl(CH$_2$)$_n$] [alkyl(C$_1$–C$_6$)O]P(=O)—,

[phenyl(CH$_2$)$_n$]—[phenyl-O P(=O)—,

[alkyl(C$_1$–C$_6$)] [phenylmethyl-O]P(=O)—,

[alkyl(C$_1$–C$_6$)O] [phenyl-O]P(=O)—,

[alkyl(C$_1$–C$_6$)O] [alkyl(C$_1$–C$_3$)$_2$N—(CH$_2$)$_n$O]—P(=O)—

[alkyl(C$_1$–C$_6$)]—P(=O)—, [phenylmethyl-O]

[CH$_3$CONH(CH$_2$)$_n$O]P(=O)—, [phenyl(CH$_2$)$_n$]

[CH$_3$CONH(CH$_2$)$_n$O]P(=O)—, [phenyl(CH$_2$)$_n$]

[4-morpholino-CO(CH$_2$)$_n$O]P(=O)—, [phenyl-O]

[(phenylmethyl-OCONH)O]—P(=O),

[alkyl(C$_1$–C$_6$)O] [Z⟨N(CH$_2$)$_n$O⟩]P(=O)—, where Z is O, S, SO or SO$_2$; n is an integer from 1 to 4; m is an integer from 2 to 4, n is an integer from 1 or 2, B is phenylmethyl, cyclohexylmethyl, alkyl (C$_1$–C$_6$), R$_{10}$ is H, alkyl(C$_1$–C$_3$), alkyl(C$_1$–C$_3$)CO—, Z is O, S, SO or SO$_2$ and q is an integer zero or one;

R$_2$ phenylmethyl, cyclohexylmethyl, —CH$_2$(2-thienyl), —CH$_2$(3-indolyl), 4-methoxybenzyl, —CH$_2$-naphthyl or lower alkyl(C$_1$–C$_6$);

R$_3$ is hydrogen or methyl;

R$_4$ is alkyl(C$_1$–C$_8$)(branched or unbranched), —(CH$_2$)$_n$—NH$_2$, phenylmethyl, cyclohexylmethyl, —X-alkyl((C$_1$–C$_8$)(branched or unbranched), X-cyclohexyl, —(CH$_2$)$_n$—X-alkyl(C$_1$–C$_3$), X—CH$_2$CH$_2$N[alkyl(C$_1$–C$_3$)]$_2$ (where X is —O— or —S—) and moieties of the formulae:

—CH$_2$C(=O)—OR$_3$, —CH$_2$C(=O)—N(R$_3$)alkyl(C$_1$–C$_3$),

—CH$_2$-(2-thienyl), —CH$_2$-(imidazolyl), —CH$_2$-(2-pyridyl)

-continued

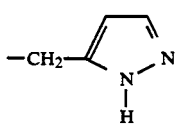

$R_5$ is hydrogen or methyl; $R_6$ is alkyl($C_1$–$C_6$), phenylmethyl, cyclohexylmethyl or

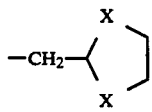

W is —O— or —N—$R_3$ and A is selected from:

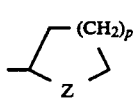

where Z is O, S, SO, $SO_2$ and p is an integer from 1 to 2, and when W is —O— then A may also be

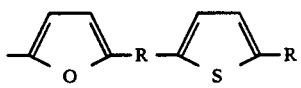

wherein R is selected from the group consisting of Cl, Br, F, —CO-lower alkyl($C_1$–$C_6$), —$CO_2$ lower alkyl($C_1$–$C_6$),

—$CO_2H$ and lower alkyl($C_1$–$C_6$).

2. A compound according to claim 1 wherein q is one and the C-terminal unit is of the formula:

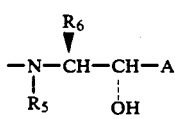

wherein $R_5$, $R_6$ and A are as defined in claim 1.

3. A compound according to claim 2 wherein the C-terminal unit is of the formula:

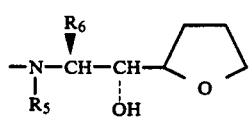

wherein $R_5$ and $R_6$ are as defined in claim 1.

4. A compound according to claim 2 wherein the C-terminal unit is of the formula:

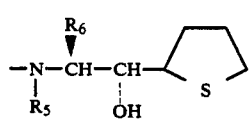

wherein $R_5$ and $R_6$ are as defined in claim 1.

5. A compound according to claim 2 wherein the C-terminal unit is of the formula:

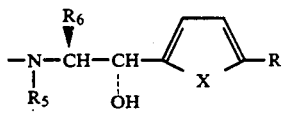

wherein $R_5$, $R_6$, X and R are as defined in claim 1.

6. A compound according to claim 3 wherein $R_1$ is

$R_2$ is (4-methoxyphenyl)methyl, $R_3$ and $R_5$ are hydrogen, $R_4$ is

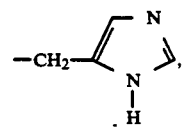

$R_6$ is cyclohexylmethyl, W is —O— and q is one.

7. A compound according to claim 3, where $R_1$ is

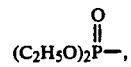

$R_2$ is phenylmethyl, $R_3$ and $R_5$ are hydrogen, $R_4$ is —$CH_2(CH_3)_2$; $R_6$ is cyclohexylmethyl, W is —NH and q is one.

8. A compound according to claim 3, where $R_1$ is

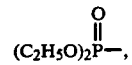

$R_2$ is (4-methoxyphenylmethyl, $R_3$ and $R_5$ are hydrogen, $R_4$ is —$SCH(CH_3)_2$, $R_6$ is cyclohexylmethyl, W is —O— and q is one.

9. A compound according to claim 3, where $R_1$ is

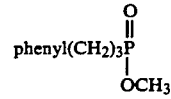

$R_3$ and $R_5$ are hydrogen, $R_4$ is —$CH_2CH(CH_3)_2$; $R_6$ is cyclohexylmethyl and q is zero.

10. A compound according to claim 3, where $R_1$ is

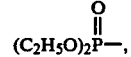

$R_2$ is cyclohexylmethyl, $R_3$ and $R_5$ are hydrogen, $R_4$ is

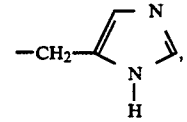

$R_6$ is cyclohexylmethyl, W is —O— and q is one.

11. A compound according to claim 3, where $R_1$ is $$(C_2H_5O)_2\overset{O}{\underset{\|}{P}}-,$$

$R_2$ is cyclohexylmethyl, $R_3$ and $R_5$ are hydrogen, $R_4$ is —$CH_2CH(CH_3)_2$, $R_6$ is cyclohexylmethyl, W is NH and q is one.

12. A compound according to claim 3, where $R_1$ is $$(phenylCH_2O)_2\overset{O}{\underset{\|}{P}},$$

$R_3$ and $R_5$ are hydrogen, $R_4$ is —$CH_2CH(CH_3)_2$, $R_6$ is cyclohexylmethyl and q is zero.

13. A compound according to claim 1, where $R_1$ is $$(C_2H_5O)_2\overset{O}{\underset{\|}{P}}-,$$

$R_2$ is phenylmethyl, $R_3$ and $R_5$ are hydrogen, $R_4$ is —$CH_2CH(CH_3)_2$, $R_6$ is cyclohexylmethyl, W is NH, q is one and A is:

<chemical structure: tetrahydrothiophene sulfone ring>

14. A compound according to claim 3, where $R_1$ is [phenyl(CH$_{23}$]

$$[CH_3CONH(CH_2)_2O]\overset{O}{\underset{\|}{P}}-,$$

$R_3$ and $R_5$ are hydrogen, $R_4$ is —$CH_2CH(CH_3)_2$ $R_6$ is cyclohexylmethyl and q is zero.

15. A compound according to claim 4, where $R_1$ is $$(C_2H_5O)_2\overset{O}{\underset{\|}{P}}-,$$

$R_2$ is phenylmethyl, $R_3$ and $R_5$ are hydrogen, $R_4$ is —$CH_2CH(CH_3)_2$, $R_6$ is cyclohexylmethyl, W is —O— and q is one.

16. A compound according to claim 3, where $R_1$ is $$(C_2H_5O)_2-\overset{O}{\underset{\|}{P}}-,$$

$R_2$ is cyclohexylmethyl, $R_3$ and $R_5$ are hydrogen, $R_4$ is —$CH_2CH(CH_3)_2$, $R_6$ is cyclohexylmethyl and W is —O— and q is one.

17. A compound according to claim 3, where $R_1$ is $$(C_2H_5O)_2\overset{O}{\underset{\|}{P}}-,$$

$R_2$ is phenylmethyl, $R_3$ and $R_5$ are hydrogen, $R_4$ is —O—$CH(CH_3)_2$, $R_6$ is cyclohexylmethyl, W is —O— and q is one.

18. A compound according to claim 4, where $R_1$ is $$(C_2H_5O)_2\overset{O}{\underset{\|}{P}}-,$$

$R_2$ is phenylmethyl, $R_3$ and $R_5$ are hydrogen, $R_4$ is

<chemical structure: -CH2-imidazole>

$R_6$ is cyclohexylmethyl, W is —O— and q is one.

19. A compound according to claim 3, where $R_1$ is $$(C_2H_5O)_2\overset{O}{\underset{\|}{P}}-,$$

$R_2$ is (4-methoxyphenyl)methyl, $R_3$ and $R_5$ are hydrogen, $R_4$ is

<chemical structure: -CH2-imidazole>

$R_6$ is cyclohexylmethyl, W is —NH and q is one.

20. A method of treating hypertension in a warm blooded animal which comprises administering to said animal a hypotensive amount of a compound selected from those of claim 1.

21. A parenteral composition of matter in dosage unit form, comprising a hypotensive amount of a compound selected from those of claim 1 in association with a parenterally acceptable carrier.

22. A process for preparing the compounds of claim 1 which comprises activating a compound of the formula:

$$R_1-W-\overset{R_2}{\underset{*}{CH}}-\overset{O}{\underset{\|}{C}}-\underset{R_3}{N}-\overset{R_4}{\underset{*}{CH}}-\overset{O}{\underset{\|}{C}}-OH$$

with a peptide coupling reagent having a suitable activating moiety selected from N,N'-dicyclohexylcarbodiimide, N,N'-dicyclohexylcarbodiimide plus N-hydroxysuccinimide, N-N'-dicyclohexylcarbodiimide plus 1-hydroxy-benzotriazol, 1-benzotriazolyl diethyl phosphate, 1-chloro-N,N-2-trimethyl-1-propen-1-amine, diphenyl phosphoryl azide, diethyl phosophorochloridate, di-loweralkyl(C$_1$-C$_8$) phosphorochloridates, diphenyl phosphorocloridate, phenyl phosphorodichloridate benzotrizol-1-yloxytris(dimethylamino)phosphonium hexafluorophosphate, N,N'bis[2-oxo-3-oxozolidinyl]phosphorodiamidic chloride, diphenylphosphinyl chloride, diethoxyphosphoryl cyanide, N,N-carbonyldiimidazole, or isobutyl chloroformate plus N-methylmorpholine, 2-chloro-1-methylpyridinium iodide, or phenyl dichlorophosphate plus imidazole to give an intermediate of the formula

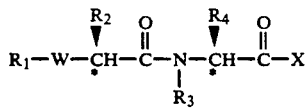

(wherein X is an activating moiety); reacting the intermediate at −10° C. to 25° C. in tetrahydrofuran, dioxane, dichloromethane or ethyl acetate with a 1-amino-2-hydroxy compound of formula

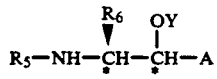

wherein Y is hydrogen or a removable blocking group selected from trimethylsilyl, t-butyldimethyl-silyl, tetrahydropyranyl, acetyl, and benzoyl and when Y is a protecting group, removing the hydroxyl protecting group.

23. A process for preparing compounds of claim 1 which comprises activating a compound of the formula

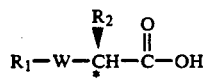

with a peptide coupling reagent having a suitable activating moiety selected from N,N'-dicyclohexylcarbodiimide, N,N'-dicyclohexylcarbodiimide plus N-hydroxysuccinimide, N-N'-dicyclohexylcarbodiimide plus 1-hydroxy-benzotriazol, 1-benzotriazolyl diethylphosphate, 1-chloro-N,N-2-trimethyl-1-propen-1-amine, diphenyl phosphoryl azide, diethyl phosophorochloridate, di-loweralkyl(C$_1$-C$_8$) phosphorochloridates, diphenyl phosphorocloridate, phenyl phosphorodichloridate benzotrizol-1-yloxytris(dimethylamino)phosphonium hexafluorophosphate, N,N'bis[2-oxo-3-oxozolidinyl]phosphorodiamidic chloride, diphenylphosphinyl chloride, diethoxyphosphoryl cyanide, N,N-carbonyldiimidazole, or isobutyl chloroformate plus N-methylmorpholine, 2-chloro-1-methyl-pyridinium iodide to give an intermediate of the formula

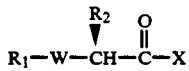

(wherein X is an activating moiety) reacting the intermediate at −10° C. to 25° C. in a solvent such as tetrahydrofuran, dioxane, dichloromethane or ethyl acetate with a compound of the formula

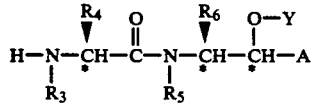

wherein Y is hydrogen or a removable blocking group of trimethylsilyl, t-butyldimethylsilyl, tetrahydropyranyl, acetyl, or benzoyl and when Y is a protecting group, removing the hydroxyl protecting group.

24. A process for preparing the compounds of claim 1 of the formula:

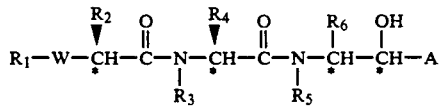

wherein a compound of the formula

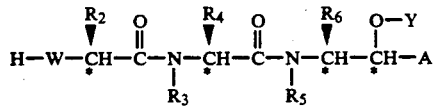

is reacted with a phosphorylating reagent of the formula

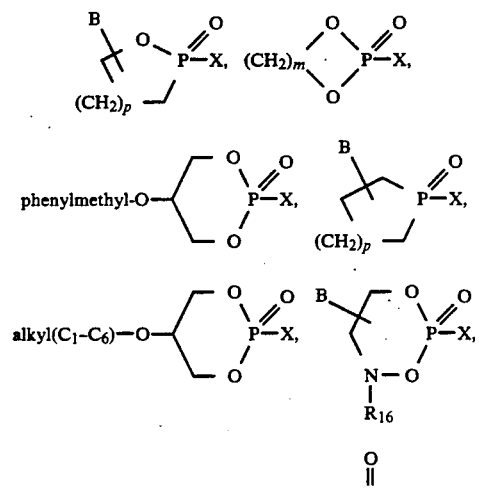

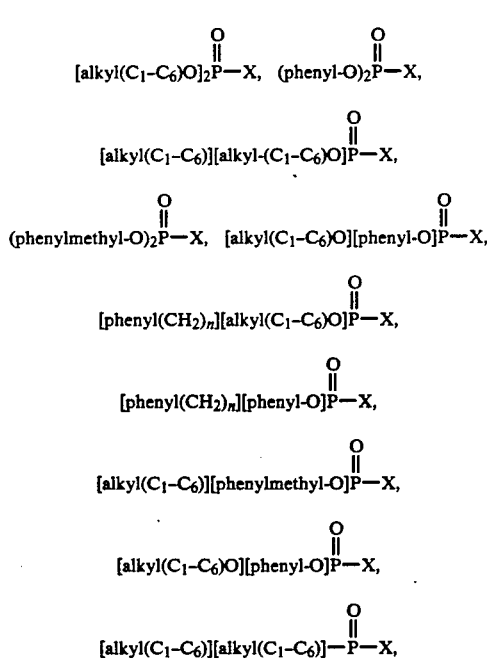

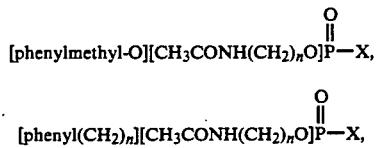

-continued

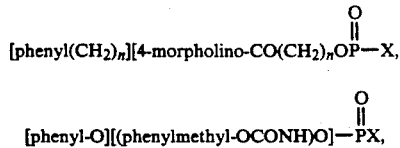

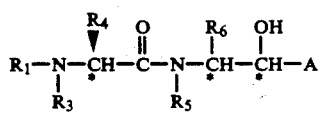

wherein X is chloro or bromo and when Y is a protecting group removing the hydroxyl protecting group.

25. A process for preparing the compounds of claim 1 of the formula:

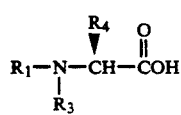

which comprises activating a compound of the formula:

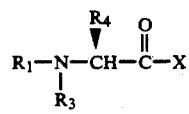

with a peptide coupling reagent having a suitable activating moiety selected from N,N'-dicyclohexylcarbodiimide, N,N'-dicyclohexylcarbodiimide plus N-hydroxysuccinimide, N-N'-dicyclohexylcarbodiimide plus 1-hydroxy-benzotriazol, 1-benzotriazolyl diethyl phosphate, 1-chloro-N,N-2-trimethyl-1-propen-1-amine, diphenyl phosphoryl azide, diethyl phosophorochloridate, di-loweralkyl($C_1$-$C_8$) phosphorochloridates, diphenyl phosphorocloridate, phenyl phosphorodichloridate benzotrizol-1-yloxytris(dimethylamino)phosphonium hexafluorophosphate, N,N'bis[2-oxo-3-oxozolidinyl]phosphorodiamidic chloride, diphenylphosphinyl chloride, diethoxyphosphoryl cyanide, N,N-carbonyldiimidazole, or isobutyl chloroformate plus N-methylmorpholine, 2-chloro-1-methylpyridinium iodide, or phenyl dichlorophosphate plus imidazole to give an intermediate of the formula

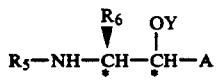

(wherein X is an activating moiety); reacting the intermediate at $-10°$ C. to $25°$ C. in tetrahydrofuran, dioxane, dichloromethane or ethyl acetate with a 1-amino-2-hydroxy compound of formula

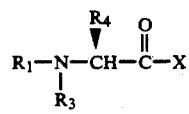

wherein Y is hydrogen or a removable blocking group selected from trimethylsilyl, t-butyldimethyl-silyl, tetrahydropyranyl, acetyl, and benzoyl and when Y is a protecting group, removing the hydroxyl protecting group.

26. A compound of the formula I:

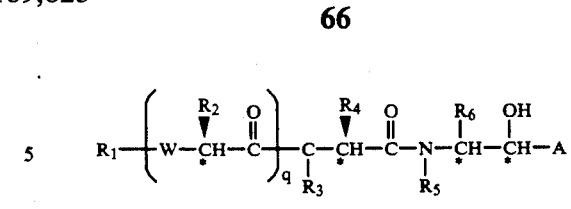

wherein
q is an integer zero or one;
$R_1$ is

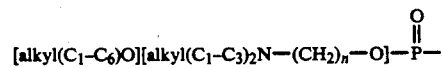

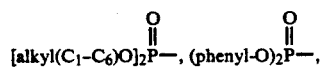

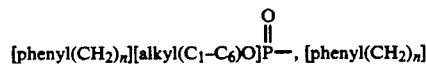

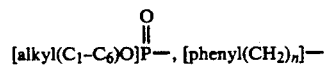

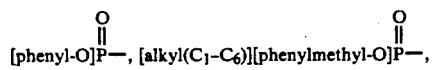

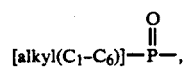

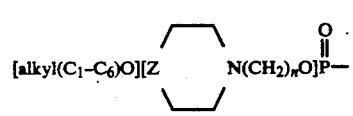

where
n is an integer from 1 to 4; and Z is O, S, SO or $SO_2$;
$R_2$ phenylmethyl, cyclohexylmethyl, 4-methoxybenzyl, $-CH_2$-naphthyl or lower alkyl($C_1$-$C_6$);
$R_3$ is hydrogen or methyl;

$R_4$ is alkyl($C_1$-$C_8$)(branched or unbranched), phenylmethyl, cyclohexylmethyl, and moieties of the formulae:

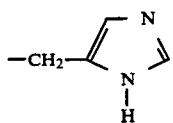

$R_5$ is hydrogen or methyl; $R_6$ is alkyl($C_1$-$C_6$), phenylmethyl, cyclohexylmethyl;
W is —O— or —N—$R_3$ and A is selected from:

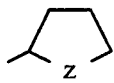

where Z is O, S, SO, $SO_2$.

27. A compound of the formula:

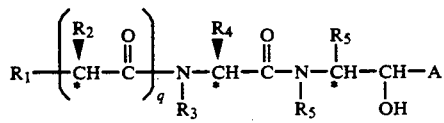

wherein q is zero or one; $R_1$ is

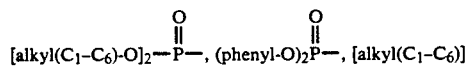

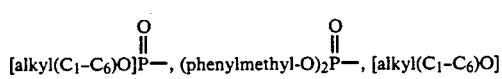

; $R_2$ is phenylmethyl, (3-indolyl)$CH_2$, (4-methoxyphenyl)methyl, cyclohexylmethyl or $CH_2$-naphthyl; $R_3$ is hydrogen; $R_4$ is alkyl($C_1$-$C_8$),

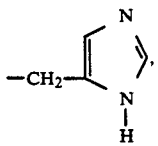

$R_5$ is hydrogen; $R_6$ is selected from the group consisting of alkyl($C_1$-$C_6$), or cyclohexylmethyl
W is O or $NR_3$; A is

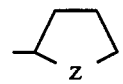

where Z is O, S, SO, $SO_2$.

28. A compound of the formula:

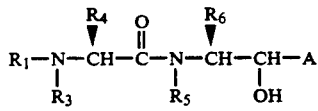

wherein
$R_1$ is

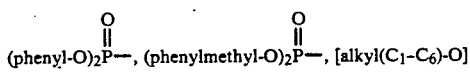

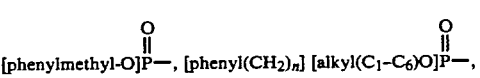

where n is an integer from 1 to 4;
$R_3$ and $R_5$ are hydrogen;
$R_4$ is alkyl($C_1$-$C_6$), O-alkyl($C_1$-$C_6$), S-alkyl($C_1$-$C_6$);

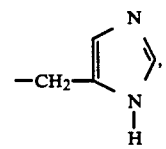

$R_6$ is cyclohexylmethyl; and
A is

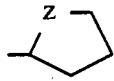

where Z is O, S, SO and $SO_2$.

29. A compound of the formula:

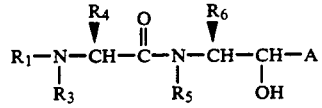

wherein
$R_1$ is

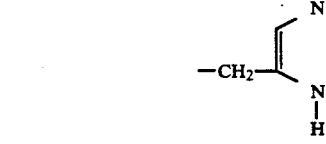

$R_3$ and $R_5$ are hydrogen;
$R_4$ is alkyl($C_1$-$C_6$), or

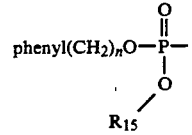

$R_6$ is cyclohexylmethyl;
$R_{15}$ is lower alkyl($C_1$-$C_3$)NH($CH_2$)$_n$—,[lower alkyl(-$C_1$-$C_3$)]$_2$ N—($CH_2$)$_n$—,phenyl($CH_2$)$_n$—, BR—($CH_2$)$_n$—, phenyl($CH_2$)$_n$NH($CH_2$)$_n$—, cyclohexyl($R_{16}$-CH)—NH($CH_2$)$_n$—, 2-pyridinyl($CH_2$)$_n$NH($CH_2$)$_n$—, 3- pyridinyl(CH₂)ₙNH(CH₂)ₙ—,
pyridinyl(CH₂)ₙNH(CH₂)ₙ—,
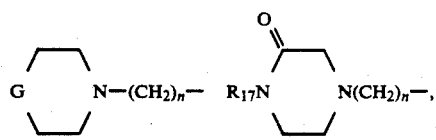
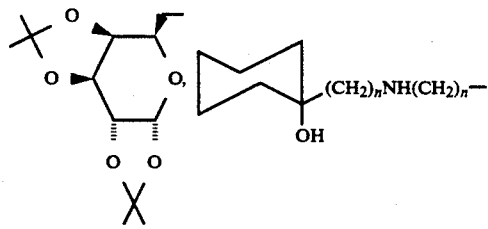
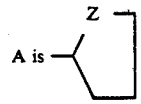
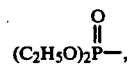
where Z is O, S, SO, SO$_2$, n is 2 or 3, G is O, S, SO, SO$_2$, NH—, CH$_3$CON—, R$_{16}$ is H or OH and R$_{17}$ is H or methyl.
30. A compound according to claim 3, where R$_1$ is
$$(C_2H_5O)_2\overset{\overset{O}{\|}}{P}-,$$
R$_2$ is —CH$_2$-naphthyl, R$_3$ and R$_5$ are hydrogen, R$_4$ is alkyl(C$_1$–C$_8$) (branched or unbranched), R$_6$ is cyclohexylmethyl, W is N—R$_3$ and q is one.
* * * * *